United States Patent
O'Connor

(10) Patent No.: US 11,574,088 B2
(45) Date of Patent: Feb. 7, 2023

(54) GRAPHICAL REPRESENTATION OF A DYNAMIC KNEE SCORE FOR A KNEE SURGERY

(71) Applicant: 360 KNEE SYSTEMS PTY LTD, New South Wales (AU)

(72) Inventor: Bede O'Connor, New South Wales (AU)

(73) Assignee: 360 KNEE SYSTEMS PTY LTD., New South Wales (AU)

( * ) Notice: Subject to any disclaimer, the term of this patent is extended or adjusted under 35 U.S.C. 154(b) by 993 days.

(21) Appl. No.: 16/308,721

(22) PCT Filed: Jun. 14, 2016

(86) PCT No.: PCT/AU2016/050483
§ 371 (c)(1),
(2) Date: Dec. 10, 2018

(87) PCT Pub. No.: WO2017/214656
PCT Pub. Date: Dec. 21, 2017

(65) Prior Publication Data
US 2019/0147128 A1    May 16, 2019

(51) Int. Cl.
*G06F 30/20* (2020.01)
*G16H 20/40* (2018.01)
*G06T 17/00* (2006.01)
*G16H 50/70* (2018.01)
*G16H 50/30* (2018.01)
*G16H 50/50* (2018.01)
*G16H 30/20* (2018.01)
*G16H 50/20* (2018.01)
*G06N 20/00* (2019.01)
*G06N 7/00* (2006.01)

(52) U.S. Cl.
CPC .............. *G06F 30/20* (2020.01); *G06N 20/00* (2019.01); *G06T 17/00* (2013.01); *G16H 20/40* (2018.01); *G16H 30/20* (2018.01); *G16H 50/20* (2018.01); *G16H 50/30* (2018.01); *G16H 50/50* (2018.01); *G16H 50/70* (2018.01); *G06N 7/005* (2013.01)

(58) Field of Classification Search
None
See application file for complete search history.

(56) References Cited

U.S. PATENT DOCUMENTS

| 7,769,763 | B1 | 8/2010 | Bem et al. |
| 2005/0197814 | A1 | 9/2005 | Aram et al. |
| 2010/0332194 | A1 | 12/2010 | Mcguan et al. |
| 2011/0029091 | A1 | 2/2011 | Bojarski et al. |
| 2013/0185310 | A1 * | 7/2013 | De Guise ............... G06F 30/20 703/11 |

OTHER PUBLICATIONS

International Search Report and Written Opinion issued in PCT/AU2016/050483, dated Jul. 15, 2016, 25 pages.

* cited by examiner

*Primary Examiner* — G Steven Vanni
(74) *Attorney, Agent, or Firm* — Kilpatrick Townsend & Stockton LLP

(57) ABSTRACT

This disclosure relates to a computer assistant for a surgeon with a graphical representation of a dynamic knee score for a knee surgery. A processor receives computer tomography data of a current patient's knee and user input from the surgeon, the user input comprises an identifier of a knee implant. The processor then retrieves multiple machine learning model parameters indicative of a machine learning performed on historical patient records. For multiple values of a rotation of the tibial component and a slope of the tibial component the processor configures a post-operative kinematic model performs a kinematic simulation and estimates a current patient outcome by applying the machine learning model. Finally, the processor generates a shaded surface spanning the multiple values of a rotation of the tibial component and a slope of the tibial component on a user interface to graphically represent the estimated current patient outcome for each of the rotation and slope.

19 Claims, 30 Drawing Sheets

300 — The next set of questions are about the symptoms you've experienced in your knee during the LAST WEEK.

301 — Do you have swelling in your knee?

302 —
- ☐ Never
- ☐ Rarely
- ☐ Sometimes
- ☐ Often
- ☐ Always

Select statistical model

| Name | Hospital | Number of patients | Cost | |
|------|----------|--------------------|------|---|
| Surgeon A | Hospital 1 | 500 | $300 | Select |
| Surgeon B | Hospital 2 | 100 | $200 | Select |
| Surgeon C | Hospital 3 | 1000 | $10,000 | Select |

Fig. 19

| One leg hanging | Weight bearing | Varus stress |
|---|---|---|
| VV: 0° IE: 0° Ligaments initial length: MCL: 62mm LCL: 65mm ACL: 40mm PCL: 50mm | VV: 3° valgus IE: 2° ext Ligaments lengthen by: MCL: -11mm LCL: -12mm ACL: -5mm PCL: -5mm | VV: 7° varus IE: 2° int Ligaments lengthen by: MCL: -14mm LCL: -6mm ACL: -5mm PCL: -5mm |

Fig. 23

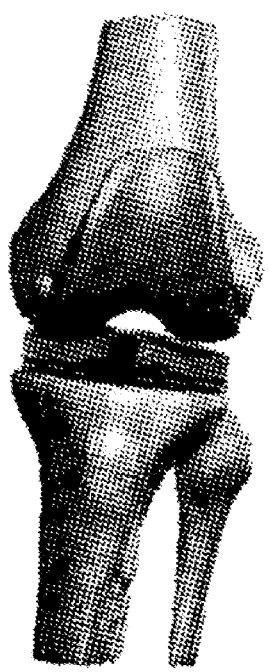  
Fig. 26a  Fig. 26b  Fig. 26c
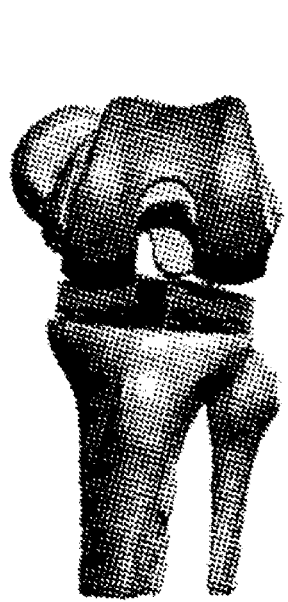 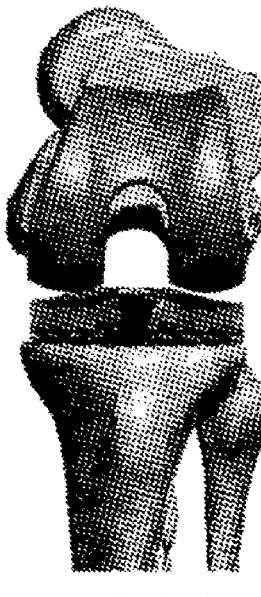 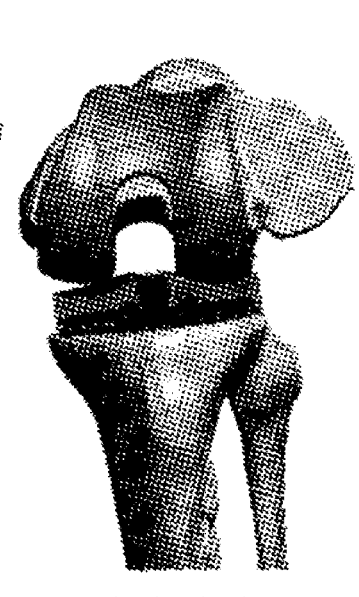
Fig. 26d  Fig. 26e  Fig. 26f

GRAPHICAL REPRESENTATION OF A DYNAMIC KNEE SCORE FOR A KNEE SURGERY

CROSS REFERENCE TO RELATED APPLICATIONS

The present application is a U.S. National Stage of International Application No. PCT/AU2016/050483 filed on Jun. 14, 2016, which is incorporated by reference in its entirety for all purposes.

TECHNICAL FIELD

This disclosure relates to a graphical representation of a dynamic knee score such as patient outcomes under different knee surgery parameters.

BACKGROUND

Osteoarthritis is the degenerative loss of cartilage tissue in a joint, and is the most common joint disease in the Australian community with approximately 15% of the population adversely affected. Of these, the knee is a common site for osteoarthritic symptoms to emerge, which can cause debilitating pain and loss of functional ability for the sufferer. Incidence increases dramatically with age, with as many as ⅓ of people showing radiographic evidence of knee osteoarthritis in the 60-69 years age group, though a smaller portion suffer symptomatically. As such, the growth in this demographic group in line with the aging population and the consequent increase in work demands placed upon this population group are contributing to an acceleration in the incidence of knee osteoarthritis across the population as a whole. Incidence is also increasing among younger age groups associated with risk factors such as obesity, joint injury and repetitive stress on the joint as a result of physical labour, further contributing to the burgeoning societal burden of knee osteoarthritis.

One treatment for end-stage knee osteoarthritis is Total Knee Replacement (TKR). One goal is to effect pain relief and recover functional ability for the sufferer. As a result of the enormous benefit that can be delivered to patients in terms of lifestyle improvement and work capability, the surgery is considered to be highly successful. The primary objective measure for success is survivor analysis with regards to revision rate, which sits at 6.5% over a 12 year window. Interestingly, this figure is vulnerable to underestimation as the conventional tracking of a patient endpoint when they undergo revision surgery implies two other success conditions: either the patient dies before undergoing a revision surgery they may require in the future or a patient's health deteriorates with age to the point where it is deemed safer not to operate even if a revision surgery is required. Nevertheless, this statistic masks a greater problem: as many as 20% of patients report dissatisfaction with the pain relief and functional outcomes of their surgery after 1 year. Due to the relative ease of data collection and hence wider adoption in joint registries of survivorship based data, as well as the relatively greater exposure of the practicing surgeon to a smaller number of highly dissatisfied patients affected by outcomes such as implant loosening than a larger number of less dissatisfied patients, there exists the potential for a bias in favour of mechanically 'safer' but not necessarily patient outcome optimal surgical decision making.

When considering survivorship with a wider range of endpoints incorporating negative pain or functional outcomes over time, the effective survivorship rate has been shown to be about half of all patients. In order to increase the success of actual patent outcomes, surgeons could make small changes in the surgery parameters. However, surgeons rarely have the tools that allow them to investigate which parameter change would have a positive impact for a particular patient.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A method for assisting a surgeon with a graphical representation of a dynamic knee score for a knee surgery comprises:

receiving computer tomography data of a current patient's knee;

receiving user input from the surgeon, the user input comprising an identifier of a knee implant;

retrieving multiple machine learning model parameters indicative of a machine learning performed on historical patient records, the historical patient records comprising multiple historical kinematic parameters of each of multiple historical patients as inputs and a reported patient outcome for each historical patient as output, the machine learning model parameters being indicative of a relationship between the multiple historical kinematic parameters and the reported patient outcome;

for each of multiple values of a rotation of the tibial component and a slope of the tibial component:
  configuring a post-operative kinematic model of the current patient's knee based on the computer tomography data, the user input and that value of the rotation and the slope;
  performing a kinematic simulation based on the post-operative kinematic model to determine multiple simulated kinematic parameters;
  estimating a current patient outcome by applying the multiple machine learning model parameters to the multiple simulated kinematic parameters of the current patient; and
generating a shaded surface spanning the multiple values of a rotation of the tibial component and a slope of the tibial component on a user interface to graphically represent the estimated current patient outcome for each of the rotation and slope.

It is an advantage that the shaded surface allows the surgeon to quickly understand the influence of rotation and slope on the patient outcome. Since the shaded surface is based on a kinematic simulation of the current patient's knee, the shaded surface is specific for the current patient. It is accurate because it determined using relationships learnt from historical patients.

The multiple historical kinematic parameters may be indicative of a kinematic simulation of the historical patient's knees.

The method may further comprise performing the machine learning on the historical patient records.

Performing the machine learning may comprise selecting the multiple historical kinematic parameters from a larger set of potential kinematic parameters.

The method may further comprise receiving from each of the multiple historical patients the reported outcome as user input via a user interface.

The multiple historical kinematic parameters and the multiple simulated kinematic parameters may be independent of the knee implant.

The method may further comprise determining one or more simulated kinematic parameters that significantly reduce the current patient outcome.

The method may further comprise generating one shaded surface for each of multiple surgery parameters by repeating the following steps for each of the multiple surgery parameters:

for each of multiple values of a rotation of the tibial component and a slope of the tibial component:
  configuring a post-operative kinematic model of the current patient's knee based on the computer tomography data, the user input and that value of the rotation and the slope and that surgery parameter;
  performing a kinematic simulation based on the post-operative kinematic model to determine multiple simulated kinematic parameters;
  estimating a current patient outcome by applying the multiple machine learning model parameters to the multiple simulated kinematic parameters of the current patient; and
generating a shaded surface spanning the multiple values of a rotation of the tibial component and a slope of the tibial component on a user interface to graphically represent the estimated current patient outcome for each of the rotation and slope.

The method may further comprise arranging the shaded surface for each of the multiple surgery parameters in a grid on a user interface to indicate combinations of surgery parameters.

The reported outcome may be based on Patient Reported Outcome Measures (PROMS).

The reported outcome may be based on a percentile within the historical patents.

The historical patient records may further comprise historical anatomical measurements and the machine learning model parameters may be indicative of a relationship between the historical anatomical measurements and the reported patient outcome and estimating the current patient outcome may comprise applying the multiple machine learning model parameters to anatomical measurements of the current patient's knee.

The historical patient records may further comprise historical demographic and patient questionnaire data capture parameters and the machine learning model parameters may be indicative of a relationship between the historical demographic and patient questionnaire data capture parameters and the reported patient outcome and estimating the current patient outcome may comprise applying the multiple machine learning model parameters to a current patient's demographic and patient questionnaire data capture parameters.

Estimating the current patient outcome may be based on kinematic expert knowledge modelled factors and beliefs to either modify or reweight penalty factors from the kinematic simulation or describing new penalty factors from the kinematic simulation.

The expert knowledge modelled factors or beliefs may be applied on an individual user basis.

The method may further comprise determining further component placement input parameters based on the simulated kinematic parameters other than tibial slope or rotation in order to optimise the estimated current patient outcome.

Software, when executed by a computer, causes the computer to perform the above method.

A computer system for assisting a surgeon with a graphical representation of a dynamic knee score for a knee surgery comprises:

data input port to receive computer tomography data of a current patient's knee;

user input device to receive user input from the surgeon, the user input comprising an identifier of a knee implant;

a data source connection to retrieve multiple machine learning model parameters indicative of a machine learning performed on historical patient records, the historical patient records comprising multiple historical kinematic parameters of each of multiple historical patients as inputs and a reported patient outcome for each historical patient as output, the machine learning model parameters being indicative of a relationship between the multiple historical kinematic parameters and the reported patient outcome;

a processor to perform for each of multiple values of a rotation of the tibial component and a slope of the tibial component:
  configuring a post-operative kinematic model of the current patient's knee based on the computer tomography data, the user input and that value of the rotation and the slope;
  performing a kinematic simulation based on the post-operative kinematic model to determine multiple simulated kinematic parameters;
  estimating a current patient outcome by applying the multiple machine learning model parameters to the multiple simulated kinematic parameters of the current patient; and
to generate a shaded surface spanning the multiple values of a rotation of the tibial component and a slope of the tibial component on a user interface to graphically represent the estimated current patient outcome for each of the rotation and slope.

The computer system may further comprise a display device to display the shaded surface to a surgeon.

A method for assisting a surgeon with a graphical representation of a dynamic joint score for a joint surgery comprises:

receiving computer tomography data of a current patient's joint;

receiving user input from the surgeon, the user input comprising an identifier of a joint implant;

retrieving multiple machine learning model parameters indicative of a machine learning performed on historical patient records, the historical patient records comprising multiple historical kinematic parameters of each of multiple historical patients as inputs and a reported patient outcome for each historical patient as output, the machine learning model parameters being indicative of a relationship between the multiple historical kinematic parameters and the reported patient outcome;

for each of multiple values of a first surgery parameter and a second surgery parameter:
  configuring a post-operative kinematic model of the current patient's joint based on the computer tomography data, the user input and that value of the first surgery parameter and the value of the second surgery parameter;

performing a kinematic simulation based on the post-operative kinematic model to determine multiple simulated kinematic parameters;

estimating a current patient outcome by applying the multiple machine learning model parameters to the multiple simulated kinematic parameters of the current patient; and outputting the estimated current patient outcome for each of the first surgery parameter and second surgery parameter.

The knee surgery may be a total knee replacement or any other knee surgery.

Optional features described of any aspect of method, computer readable medium or computer system, where appropriate, similarly apply to the other aspects also described here.

BRIEF DESCRIPTION OF DRAWINGS

An example will now be described with reference to:

FIG. 9 illustrates an example pre-operative patent questionnaire.

FIG. 19 illustrates a model selection user interface.

FIG. 23 illustrates a mechanical model of a knee under three different mechanical loads.

FIGS. 26a to 26f graphically illustrate the predicted characteristic of the knee after surgery.

DESCRIPTION OF EMBODIMENTS

This disclosure provides a system that generates a graphical display for a surgeon to show the surgeon in which direction the surgery parameters could be changed in order to improve the patient outcome. The display is calculated based on the current patients computer tomography (CT) scan or other medical imaging data and mechanical simulation fed into a trained machine learning model. The machine learning model links mechanical simulations of historical patients to their respective reported patient outcomes, which makes the prediction or estimation for the current patient and the different surgery parameters accurate.

Figure 1:
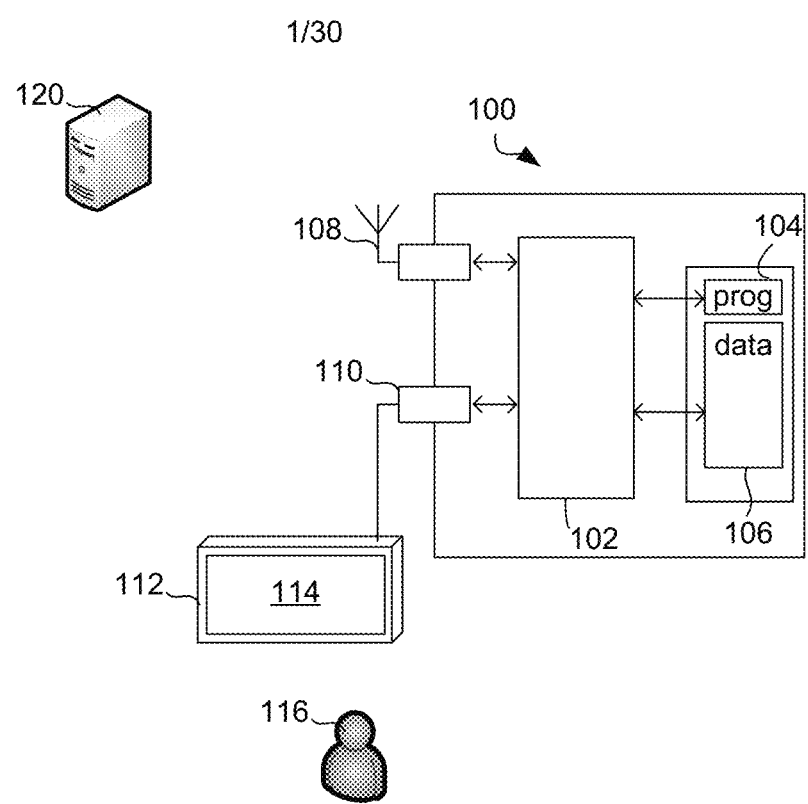
FIG. 1 illustrates a computer system for assisting a surgeon.

FIG. 1 illustrates a computer system 100 for assisting a surgeon with a graphical representation of a dynamic knee score for a knee surgery. The computer system 100 comprises a processor 102 connected to a program memory 104, a data memory 106, a communication port 108 and a user port 110. The program memory 104 is a non-transitory computer readable medium, such as a hard drive, a solid state disk or CD-ROM. Software, that is, an executable program stored on program memory 104 causes the processor 102 to perform the method in FIG. 2, that is, processor 102 receives 202 computer tomography (CT) data of a current patient's knee from a CT imaging machine 120. For example, processor 102 receives CT images of multiple slices through the knee and builds a 3D model of the particular knee joint of this current patient.

Processor 102 further receives 204 user input from the surgeon, such as through a user interface. The user input comprises an identifier of a knee implant. Processor 102 can access a database of knee implants to retrieve the geometries and recommended surgery parameters of the chosen knee implant. In some examples, most surgery parameters are defined in the database but the particular surgery parameters rotation and slope of the tibial component are often less restricted and/or varied substantially by each surgeon.

Processor 102 can then perform the planned surgery virtually. That is, processor 102 changes the 3D shape of the bones by introducing cut surfaces and adding the shape of the selected implants according to the surgery parameters from the database. Processor 102 can derive a kinematic model, which is a simplified representation that disregards the 3D details that are not needed when considering the movement of the knee joint. In other words, processor 102 configures a post-operative kinematic model by virtually performing the operation and simplifying the 3D model to the kinematic model. The kinematic model comprises joints, bearing/contact surfaces, tension elements, members etc. Processor 102 can then use the kinematic model to perform a simulation of the post-operative knee joint as described in more detail below. In particular, processor 102 may perform a movement of the knee joint, that is processor 102 iteratively changes the angle between tibia and femur and calculates for each angle the multiple kinematic parameters. Processor 102 may also aggregate parameters from the multiple angles into one parameter, such as maximum or average. This way, the kinematic simulation outputs a number of kinematic parameters that may comprise the following:

| Measure | Description |
| --- | --- |
| Anterior.MCL | Strain in the anterior Medial Collateral Ligament |
| Anterior.PCL | Strain in the anterior Posterior Cruciate Ligament |
| AntMCL.len | Length of the anterior Medial Collateral Ligament |
| AntPCL.len | Length of the anterior Posterior Collateral Ligament |
| Femoral.Rollback | Posterior drift of the transepicondylar axis relative to the tibial M-L axis |
| FemoralMLShift | Medial/Lateral shift of the femoral component axis relative to the tibial |
| Flexion | Flexion of the femur to tibia |
| IE.Rotation | Rotation of the transepicondylar axis relative to the tibial insert axis and frame |
| IECoC | Rotation of the femoral component relative to the tibial |
| Lateral.FFC | Anterior/posterior drift of the lateral flexion facet centre |
| LCL | Strain in the Lateral Collateral Ligament |
| LCL.len | Length of the Lateral Collateral Ligament |
| Medial.FFC | Anterior/posterior drift of the medial flexion facet centre |
| MLCompartment.Torq | Medial-lateral torque across the tibial insert |
| Patella.Lat.Shift | Patella lateral displacement relative to femoral axis |
| Patella.Lat.Tilt | Patella lateral tilt relative to femoral axis |
| Patella.Shear | Patella lateral directional force relative to femoral axis |
| PatFlexion | Patella 'flexion'/foretilt relative to tibial axis |
| patLatShiftCoC | Patella button lateral displacement relative to tibial axis |
| patLatTiltCoC | Patella button lateral tiltt relative to tibial axis |
| PatPackingForce | Patella-femoral force down the patella's symmetrical axis |
| Posterior.MCL | Strain in the posterior Medial Collateral Ligament |
| Posterior.PCL | Strain in the posterior Posterior Cruciate Ligament |
| PostMCL.len | Length of the posterior Medial Collateral Ligament |
| PostPCL.len | Length of the posterior Posterior Collateral Ligament |
| Quad.Force | Force exerted/resisited by the quadriceps tendon |
| rollbackCoC | Anterior/posterior drift of the flexion facet centre axis |
| TibAPShear | Femor-tibial shearing force in the anterior direction |
| TibMLShear | Femor-tibial shearing force in the medial direction |
| TibZForce | Tibia-femoral force down the tibia's mechanical axis |
| Varus | Coronal plane alignment of the bones |
| VarusCoC | Coronal plane alignment of the femur and tibia |

These measurements create time series that may be deconstructed into single parameters in a variety of ways, such as maxima and minima over the flexion cycle, the value of flexion measure at the kinematic maxima or minima, in fixed 15 degree increments of flexion or by taking the difference between each set of fixed 15 degree increments.

Once the kinematic parameters are calculated, the surgeon may perform the planned knee surgery, that is perform knee replacement with the selected knee implant.

Figure 7:
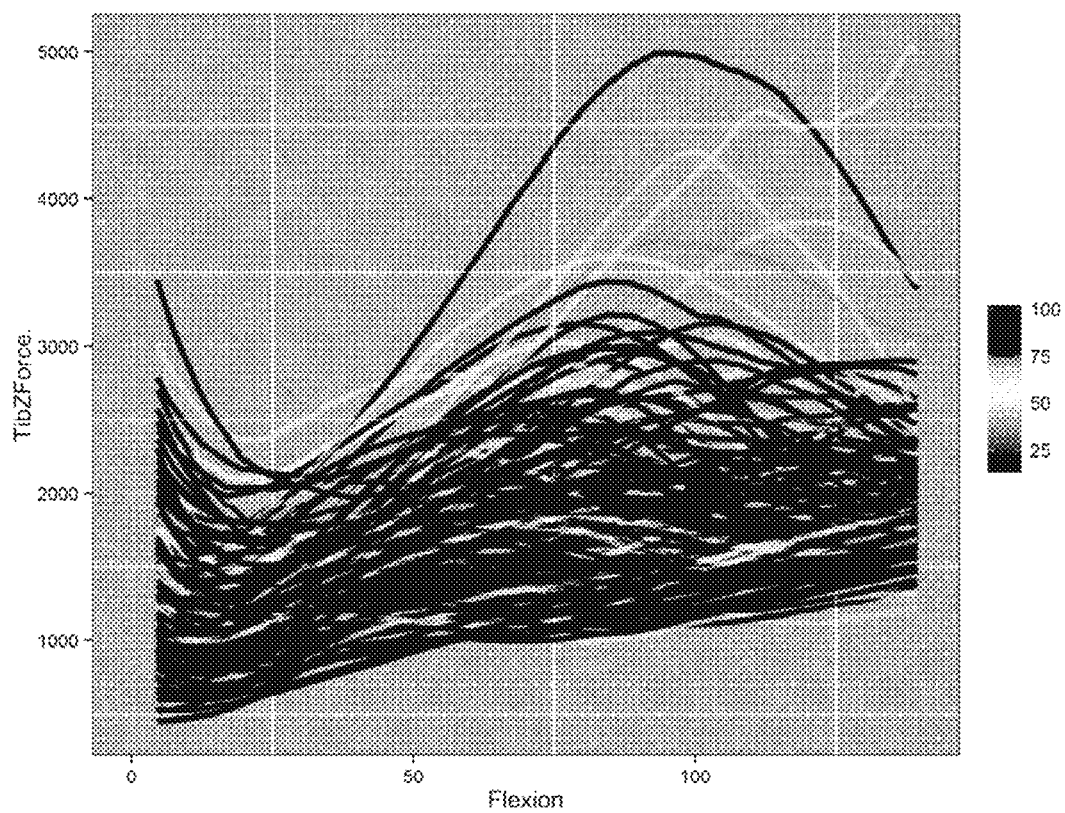
FIG. 7 illustrates the Tibial Z Force over Flexion angle for various different pain scores.

After the operation, the patient can fill-in a electronic questionnaire on an electronic computer device with multiple questions displayed on a user interface as shown in FIG. 7. The questions relate to the patient outcome of the operation, such as pain levels, flexibility and other objective or subjective measures as described in more detail below. As the patient answers the questions, processor 102 stores the answers to create a reported patient outcome stored on data memory 106. In one example, processor 102 calculates a single score, that is, a value that represents the patient outcome. For example, processor 102 calculates a single pain score where a lower pain score is preferable. As a result, processor 102 can store the reported patient outcome, such as the pain score, associated with the determined kinematic parameters. This data can serve as a sample for a supervised learning algorithm where the kinematic parameters are the inputs and the reported patient outcome is the output variable.

Processor 102 performs the above steps for multiple historical patients to create multiple historical patient records that each comprise the multiple historical kinematic parameters of each of multiple historical patients as inputs and a reported patient outcome for each historical patient as output. On these historical patient records processor 102 may perform a machine learning method, such as a linear regression multivariate adaptive regression spline modelling, neural network modelling, tree augmented naïve Bayesian modelling, support vector machines or decision tree modelling. The machine learning method produces machine learning parameters that are indicative of the relationship between the multiple historical kinematic parameters and the reported patient outcome. For example, the machine learning model parameters may be weights of a weighted sum of the kinematic parameters, such that the result of the weighted sum is an estimate or prediction of the patient outcome. The machine learning method may comprise a feature selection step such that the number of machine learning model parameters is significantly less than the kinematic parameters, such as four machine learning model parameters for 34 kinematic parameters. The machine learning model parameters may be pre-calculated and stored on data memory 106, from where processor 102 retrieves them in step 206. For example, the machine learning model parameters may be stored in an SQL database and processor 102 performs an SQL query on that database.

The machine learning may be performed only on the kinematic parameters, which means the kinematic parameters are independent from the implant geometry and other implant characteristics. This has the advantage that the learned machine model parameters can be applied to many different implants without the need for re-training the model for each implant.

Based on the historical data and the machine learning model parameters that are calculated using the historical patient data, the aim is to predict a patient outcome for a current patient before the surgery.

Often, most of the surgery parameters are provided by the manufacturer of the selected implant with little room for variation. In one example the two parameters of rotation of the tibial component and slope of the tibial component can be varied by the surgeon more freely than the other parameters. Therefore, it would be useful for the surgeon to see how a change in those parameters will affect the patient outcome. Therefore, processor 102 uses the machine learning model to predict the outcome for each of multiple combinations of rotation and slope. In other words, processor 102 samples the value space of rotation and slope. In one example, processor 102 uses five samples, four of which are located at the combinations of extreme values (minSlope|minRot, minSlope|maxRot, maxSlope|minRot, maxSlope|maxRot) and one is located in the centre of the value space 0.5(maxSlope-minSlope)|0.5(maxRot-minRot). Other sampling strategies may equally be employed, such as grid-based sampling, Monte Carlo sampling or gradient based sampling.

For each sample, processor 102 configures 208 a post-operative kinematic model of the current patient's knee based on the computer tomography data, the user input and that value of the rotation and the slope. This means the geometry of the selected implant is reflected in the kinematic model as well as the slope and rotation from the current sample. The calculated kinematic parameters should accurately reflect the physical properties of the patient's knee if the surgery would proceed with the rotation and slope from the current sample.

Processor 102 then performs 210 a kinematic simulation based on the post-operative kinematic model to determine multiple simulated kinematic parameters in the same way as the training samples for the machine learning were calculated above.

Processor 102 then estimates 212 a current patient outcome by applying the multiple machine learning model parameters to the multiple simulated kinematic parameters of the current patient. For example, processor 102 selects the parameters as identified by the feature selection step of the machine learning method. Processor 102 may then calculate the weighted sum of those selected parameters in the example of a linear model. This way, processor 102 calculates multiple estimated or predicted patient outcomes. That is, processor 102 calculates one estimated or predicted patient outcome for each combination of rotation and slope parameters.

Finally, processor 102 generates 214 a shaded surface that spans the multiple values of a rotation of the tibial component and a slope of the tibial component on a user interface to graphically represent the estimated current patient outcome for each of the rotation and slope. For example, processor 102 may calculate grey scale values from 0 (black) to 255 (white) by assigning the minimum patient outcome to 0 (black) and the maximum to 255 (white) and interpolating in between and may therefore generate a linear gradient. Other interpolations, such as polynomial or spline may equally be applicable.

Figure 3:
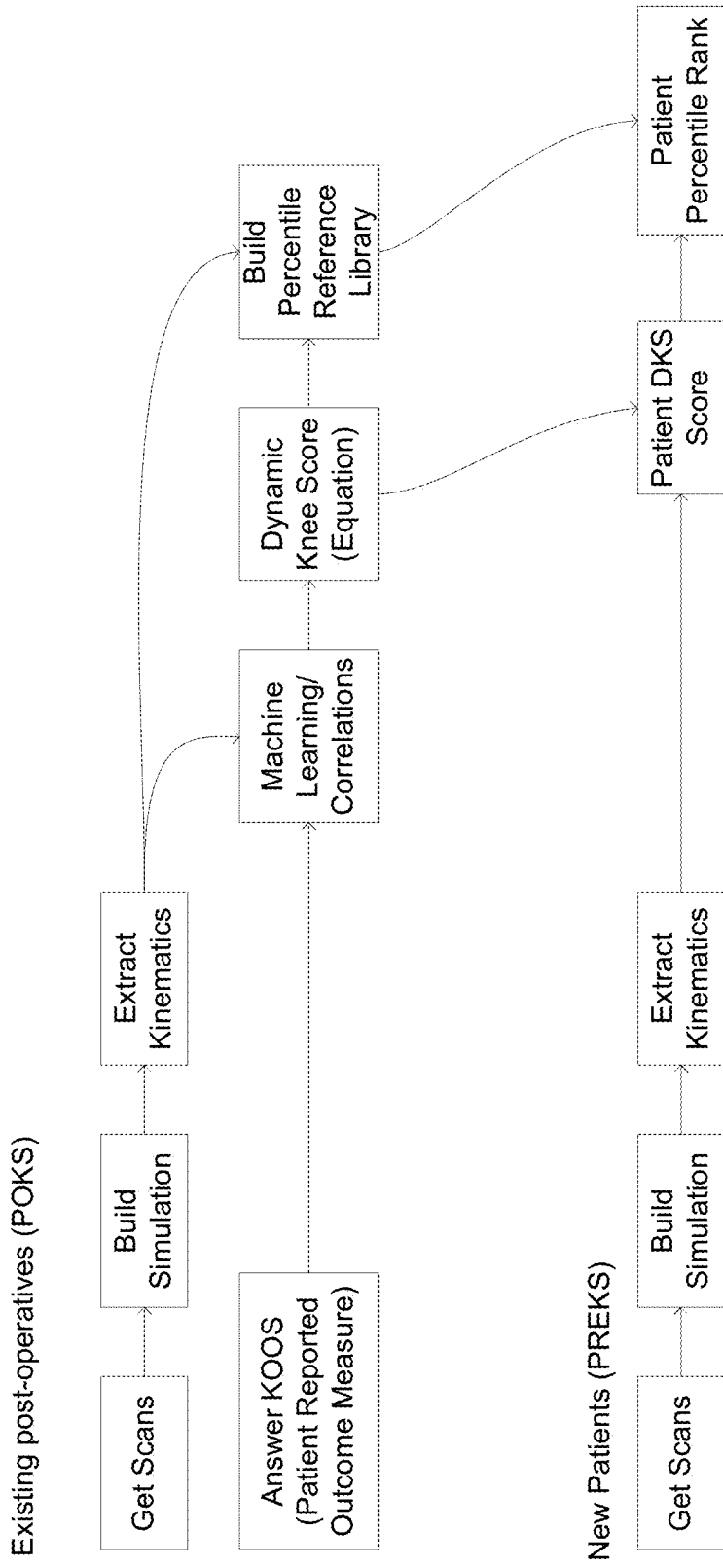
FIG. 3 illustrates a flowchart of a machine learning architecture.

FIG. 3 illustrates a flowchart of the machine learning on existing post-operative data sets and the prediction for new patients.

Figure 4A:
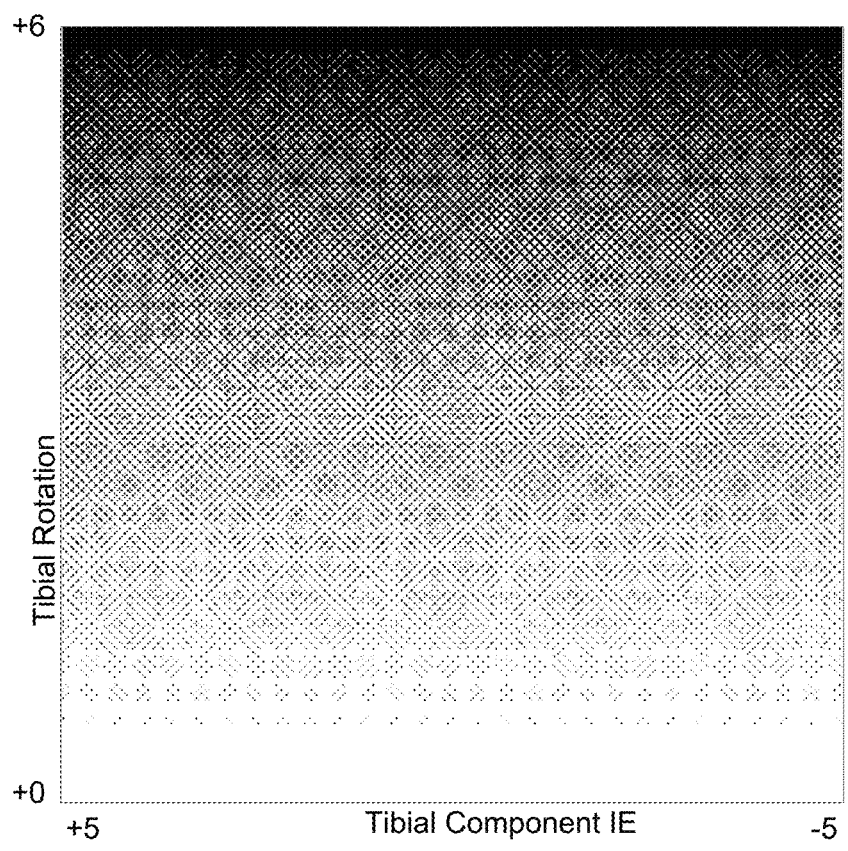
FIGS. 4a and 4b illustrate example shaded surfaces.
Figure 4B:
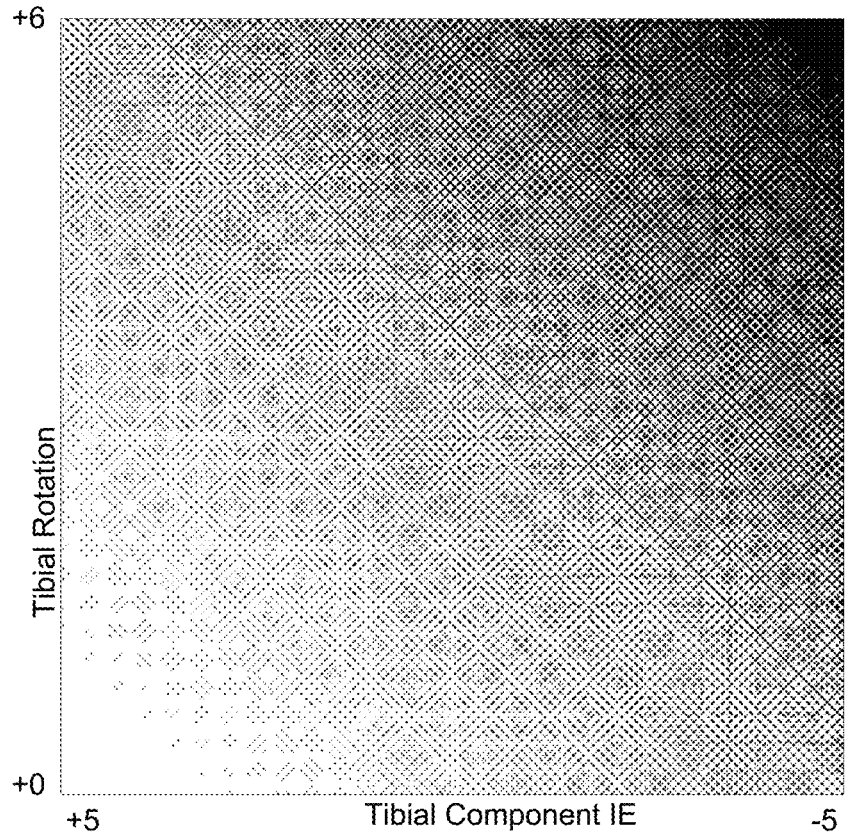

FIG. 4a illustrates an example shaded surface generated by method 200. The horizontal axis indicates tibial component slope and the vertical axis indicates tibial rotation. In this example, the surgeon can see that the slope has little effect while the rotation should be at a minimum to improve the surgery outcome. FIG. 4b illustrates another example where rotation should be at a minimum while slope should be at a maximum. While a surgeon may not want to use these extreme values, the surgeon can see that changing the slope and rotation slightly towards the optimum values will likely improve the outcome.

In one example, processor 102 normalises the patient outcomes, such that a low percentile, such as $10^{th}$ percentile, is assigned to black and a high percentile, such as $90^{th}$ percentile is assigned to white. These percentiles relate to the historical training data. For example, if the pain score ranges from 0 (no pain) to 10 (extreme pain) and the $90^{th}$ percentile is 9 and the $10^{th}$ percentile is 1. Then, if the current patient outcomes for five different combinations of rotation and slope are 7, 8, 8, 9, 10, the gradient surface would be relatively dark with no light or white areas indicating to the surgeon that all combinations have a relatively undesirable outcome. However, the lightest area would be for value 7 and the surgeon can choose the corresponding slope and rotation to achieve this value. In a different example, where the predicted current patient outcomes are 5, 2, 0, 3, 10 the shaded surface would have a clear white area and the surgeon can choose the slope and rotation corresponding to that area.

Processor 102 may then store the shaded surface, such as it the form of an image file (JPEG, GIF, SVG, BMP, etc.) on data store 106, such as on RAM or a processor register. Processor 102 may also send the shaded surface via communication port 108 to a server, such as patient management database. Processor 102 may include the shaded surface into a website. In yet another example, processor 102 generates an electronic document, such as a PDF file including the shaded surface. In all examples, the shaded surface may include labels of the axes with number values for corresponding values of rotation and slope. In one example the shaded surface may be stored parameterised, such as in the form of a JavaScript object that renders the surface on a user interface.

Figure 5:
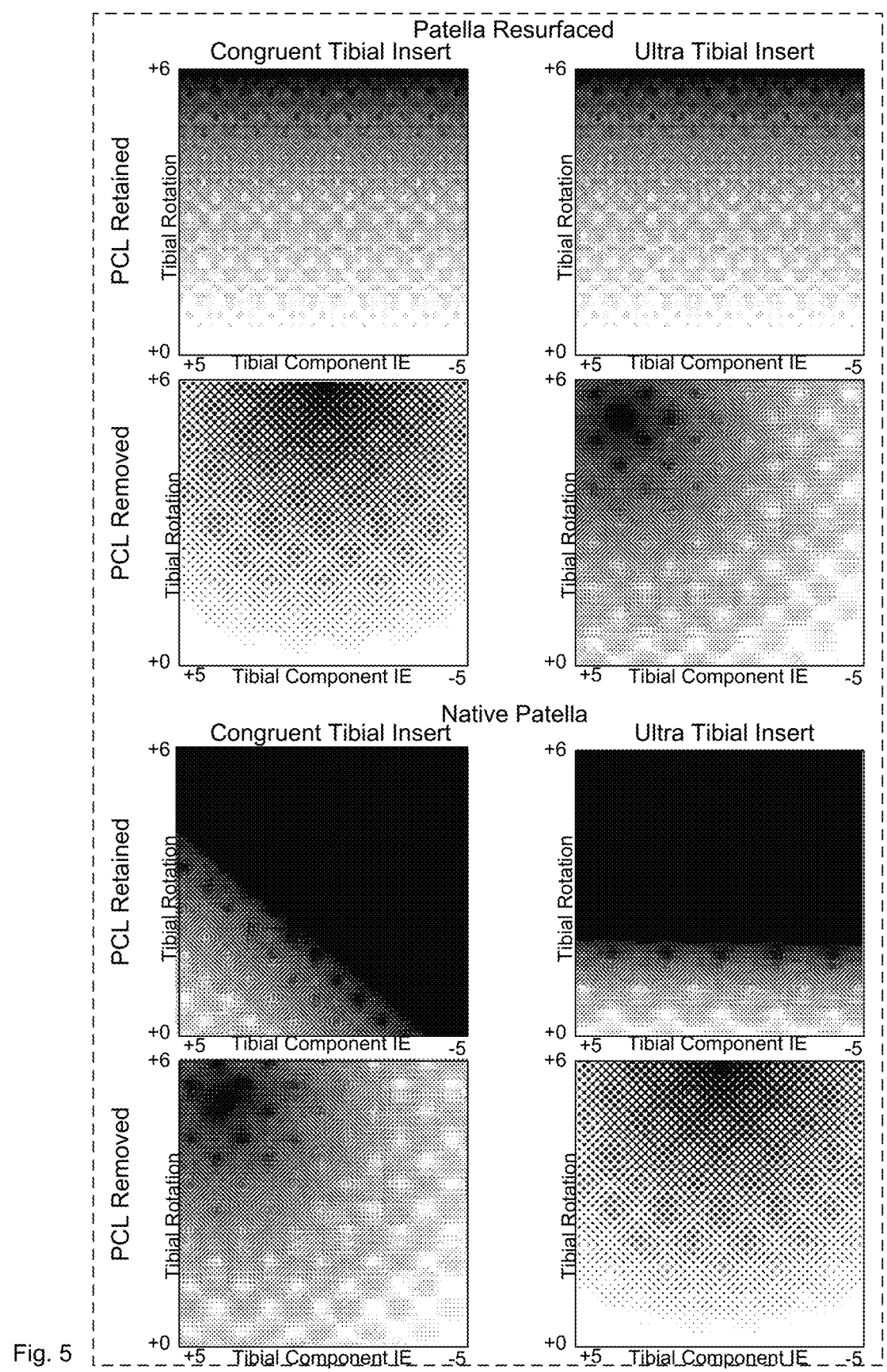
FIG. 5 illustrates multiple shaded surfaces corresponding to different combinations of surgical parameters.

Processor 102 may repeat the steps of configuring and simulating the kinematic model, predicting multiple outcomes and generating the shaded surface for multiple surgery parameters, such as PCL removed/retained, patella resurfaced/unresurfaced, Insert congruent/ultra. This way, processor 102 generates multiple shaded surfaces as illustrated in FIG. 5. In the case of multiple surgery parameters, processor 102 generates a shaded surface for each combination and may arrange the shaded surfaces in a grid pattern on the user interface similar to a Karnaugh diagram. This is particularly useful for binary surgery parameters, such as yes/no options. A surgeon can inspect the various shaded surfaces and can see which combination shows light areas for certain values of rotation and slope. The surgeon can then chose the binary parameters to select the shaded surface and then chose rotation and slope to select the white area in the shaded surface. The shaded surfaces as shown in FIG. 5 may be displayed on a tablet computer, monitor or printed. The generation of the shaded surfaces may be integrated into an interactive software tool or 'app' where the surgeon can change one parameter and the tool re-calculates the shaded surface according to method 200 in FIG. 2.

In one example, the shaded surface is in colour and instead of a 0 to 255 grey scale value, processor interpolates a value range that maps to green for 0 and red for 255 or other colour values.

Further Improvements

Figure 6:
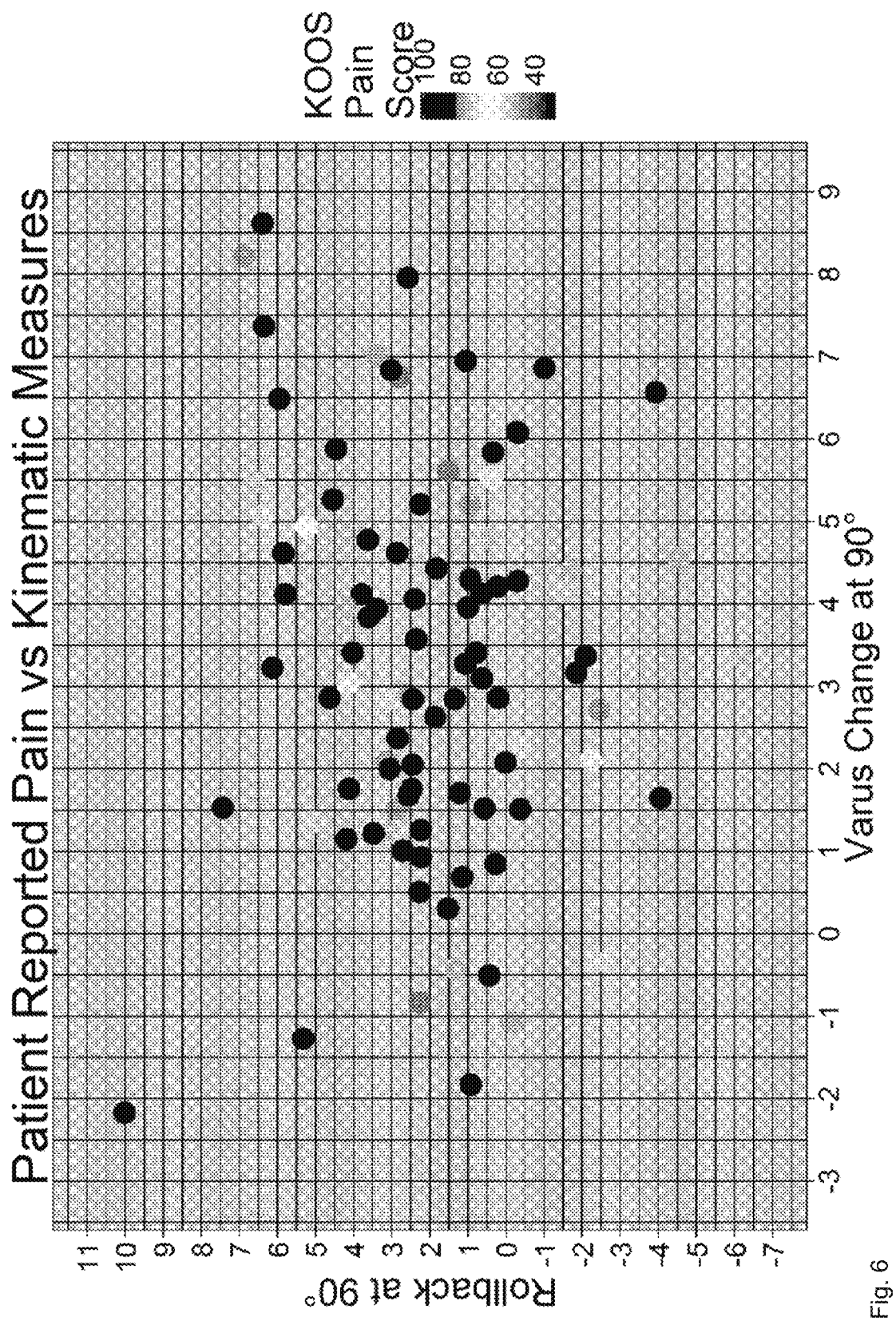
FIG. 6 illustrates an example scatter plot.

In one example, processor determines 102 one or more simulated kinematic parameters that significantly reduce the current patient outcome. For example, processor 102 selects one particular kinematic parameter that is most responsible for a bad estimated outcome. This can be particularly useful, where the entire shaded area is black or red and the surgeon can use additional information to improve the outcome. For example, the surgeon can change surgical parameters with very little opportunity for variation provided by the implant manufacturer. Processor 102 may select that most responsible kinematic parameter by ranking the summands of the weighted sum and outputting the largest summand, that is, after multiplication by the corresponding machine learning model parameter. FIG. 6 illustrates an example scatter plot output where samples are plotted on a varus change axis and a rollback axis. The darkness of the dots indicates the simulated pain score. From this plot, the surgeon can see that most patients with a good pain score (close to 100) are centred around rollback=2 and varus change=3.

FIG. 7 illustrates the Tibial Z Force over Flexion angle for various different pain scores.

In yet another example, processor 102 performs a sensitivity analysis between the parameters of the kinematic model and the patient outcome to determine which of the parameters of the kinematic model can be changed to improve the patient outcome significantly.

In one example, the historical patient records, that is, the training samples, further comprise historical anatomical measurements. In this example, the machine learning model parameters are indicative of a relationship between the historical anatomical measurements and the reported patient outcome. Estimating the current patient outcome then comprises applying the multiple machine learning model parameters to anatomical measurements of the current patient's knee. Anatomical measurements may include one or more of the long leg varus/valgus alignment, the transepicondylar to posterior condylar axes angle, the Whiteside's axis to posterior condylar axes angle, the distal and posterior offset of each ligament (native and implanted), the posterior condylar offset ratio, the femoral joint line angle, the tibial joint line angle, the long leg joint line angle, the femoral neck anteverion to other axes, the femoral anatomic to mechanical axis deviation, the trochlear groove depth, the femoral bow, the q angle, the transmaleolar or tibial torsion angle or insall-salvati's ratio.

In another example, the historical patient records further comprise historical demographic and patient questionnaire data capture parameters. In this example, the machine learning model parameters are indicative of a relationship between the historical demographic and patient questionnaire data capture parameters and the reported patient outcome. Estimating the current patient outcome then comprises applying the multiple machine learning model parameters to a current patient's demographic and patient questionnaire data capture parameters. The demographic and patient questionnaire data capture parameters may comprise age, gender, occupation, current knee pain state, current knee related activity impairment state, other musculoskeletal impairment and pain and subjectively measured anxiety and depression scores.

In a further example, estimating the current patient outcome is based on kinematic expert knowledge modelled factors and beliefs to either modify or reweight penalty factors from the kinematic simulation or describing new penalty factors from the kinematic simulation. This allows experts including the surgeon or other kinematic experts to adjust the weights that the kinematic factors have in the machine learning model. This may also include a review of published literature on knee surgeries. Processor 102 may generate a user interface that displays the current factors and allows a user to adjust them.

The expert knowledge modelled factors or beliefs may be applied on an individual user basis, which means that an individual surgeon or hospital or other group may apply those factors to their patients which either gives them a competitive advantage in better outcomes or accommodates different opinions from different surgeons or locally observed inherent population response differences.

While the above examples relate to only rotation and slope of the tibial component, it is to be understood that processor 102 may determine different or further component placement input parameters based on the simulated kinematic parameters other than tibial slope or rotation in order to optimise the estimated current patient outcome.

Computer Architecture

It is noted that processor 102 may receive data, such as CT image data, from data memory 106 as well as from the communications port 108 and the user port 110, which is connected to a display 112 that shows a visual representation 114 of the CT data to a surgeon 116 or other user or operator. Processor 102 may also receive the CT image data from a CT imaging machine directly through a direct data connection or through a data network, such as the internet. In one example, processor 102 receives image data from an X-ray, magnetic resonance imaging (MRI) or computer tomography (CT) imaging device via communications port 108, such as by using a Wi-Fi network according to IEEE 802.11. The Wi-Fi network may be a decentralised ad-hoc network, such that no dedicated management infrastructure, such as a router, is required or a centralised network with a router or access point managing the network. Processor 102 may also be connected to a data source to retrieve machine learning model parameters from the data source, which may be hosted on data memory 106 or on a database hosted by computer system 100 or externally and accessible by processor 102 over a data network.

Although communications port 108 and user port 110 are shown as distinct entities, it is to be understood that any kind of data port may be used to receive data, such as a network connection, a memory interface, a pin of the chip package of processor 102, or logical ports, such as IP sockets or parameters of functions stored on program memory 104 and executed by processor 102. These parameters may be stored on data memory 106 and may be handled by-value or by-reference, that is, as a pointer, in the source code.

The processor 102 may receive data through all these interfaces, which includes memory access of volatile memory, such as cache or RAM, or non-volatile memory, such as an optical disk drive, hard disk drive, storage server or cloud storage. The computer system 100 may further be implemented within a cloud computing environment, such as a managed group of interconnected servers hosting a dynamic number of virtual machines.

It is to be understood that any receiving step may be preceded by the processor 102 determining or computing the data that is later received. For example, the processor 102 determines measurement data and stores the measurement data in data memory 106, such as RAM or a processor register. The processor 102 then requests the data from the data memory 106, such as by providing a read signal together with a memory address. The data memory 106 provides the data as a voltage signal on a physical bit line and the processor 102 receives the measurement data via a memory interface.

It is to be understood that throughout this disclosure unless stated otherwise, nodes, edges, graphs, solutions, variables, surgery plans, dimensions, locations and the like refer to data structures, which are physically stored on data memory 106 or processed by processor 102. Further, for the sake of brevity when reference is made to particular variable names, such as "predicted characteristic" or "spatial parameter of the surgery" this is to be understood to refer to values of variables stored as physical data in computer system 100.

Figure 2:
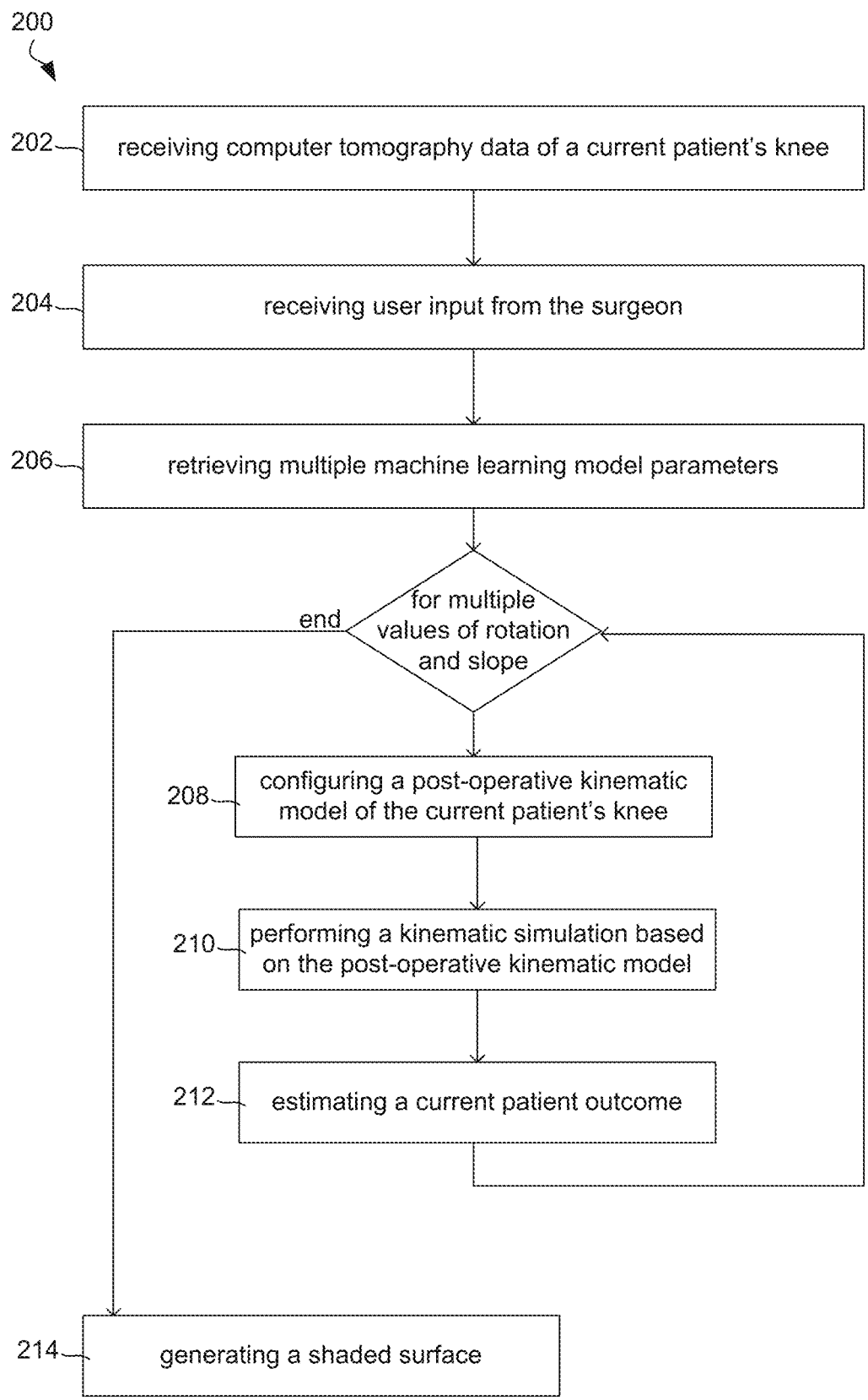
FIG. 2 illustrates a method for assisting surgery of a knee.

FIG. 2 illustrates a method 200 as performed by processor 102 for assisting surgery of a joint. FIG. 2 is to be understood as a blueprint for the software program and may be implemented step-by-step, such that each step in FIG. 2 is represented by a function in a programming language, such as C++ or Java. The resulting source code is then compiled and stored as computer executable instructions on program memory 104.

Reported Patient Outcomes

The following disclosure provides details on reported patient outcomes. While examples including Bayesian Networks and expert knowledge capture are provided, it is noted that the methods disclosed herein for machine learning of patient outcomes given mechanical simulation parameters are applicable to less complex cases, such as a single pain score or standardised Patient Reported Outcomes Measures (PROMS).

Figure 8:
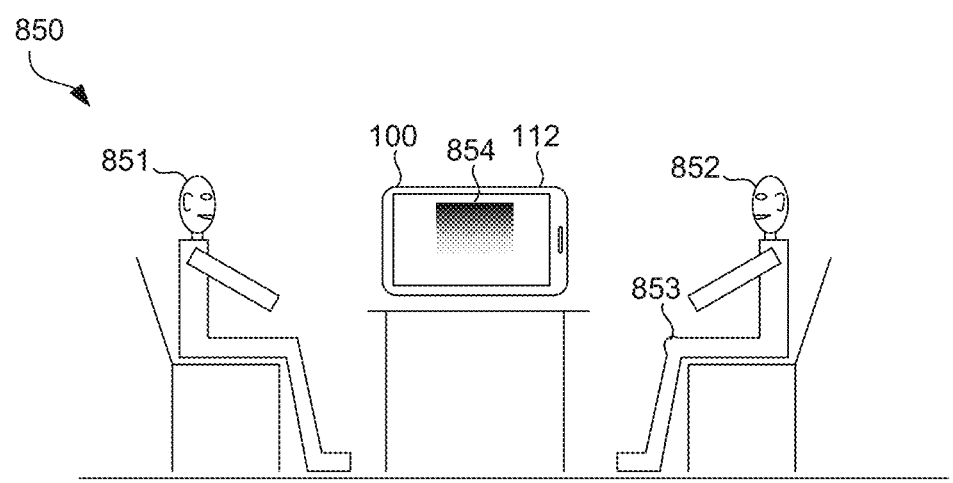
FIG. 8 illustrates a surgeon's consulting room

FIG. 8 illustrates a surgeon's consulting room 850 where the computer system 100 of FIG. 1 is in use. Present in the room 850 are the surgeon 851 and the patient 852 with a swollen knee 853 that needs surgery. At the moment schematically captured in FIG. 8 patient 852 has provided patient input data to the computer device 100, that is a tablet computer in this example, and the processor 102 of the device 100 has calculated a predicted outcome value. Processor 102 has also generated an electronic document comprising a report and displays the electronic document on screen 112 of tablet 100. In particular, processor 102 generates, as part of the report, a shaded surface 854. Surgeon 851 can now discuss the value 854 with patient 852, which allows surgeon 851 to make changes to the operation procedure, care plan or manage the patient's 852 expectations to increase the chances of a positive outcome.

FIG. 9 illustrates an example pre-operative patent questionnaire user interface 900 displayed on touch screen 112. The questionnaire interface 900 may be web-based, which means processor 102 is part of a web-server and generates the questionnaire interface 900 by writing HTML code to a data store that is accessible by a browser running on a patient device, such as a tablet computer. In another example, the questionnaire interface 900 is app-based, which means an app is installed on computer system 100 and processor 102 generates the questionnaire interface 900 by executing library functions that contain generic user interface functions.

FIG. 9 shows one page of the questionnaire 900 and the current page contains exactly one question 901 with multiple possible answers 902. Processor 102 monitors user interaction with respect to the user interface 900 and upon detecting user interaction with one of the multiple possible answers 902, processor 102 registers this answer and creates the next page of the questionnaire that again contains only a single question.

Processor 102 may register the selected answer by storing an answer value on data store 106, such as '1' if the patient selected 'Never', '2' if the patient selected 'Rarely' and so on. In the web-based example processor 102 sends the answer value to a server via XMLHttpRequest, POST or GET methods.

As a next step, processor 102 receives patient input data indicative of answers of a patient in relation to the preoperative patient questionnaire. This may mean the processor 102 receives the answer values from data store 106 or from a web-based interface via XMLHttpRequest, POST or GET methods. The patient input data may be identical to the answer values or may be pre-processed, such as by compression or encryption to obtain the patent input data.

In some examples, the patient input data is generated by a patient sensor and uploaded to the computer system 100. For example, the patient can wear a step counting device, such as a smart phone with a step counting app installed or a wrist or ankle sensor. Processor 102 then receives the step count from the step sensor and uses the step count just as the questionnaire data as if the patient had been asked about their activity level and answered in the number of steps.

Processor 102 then feeds the received patient input data into a statistical model to evaluate 203 the statistical model. This way, processor 102 determines a predicted satisfaction value indicative of satisfaction of the patient with the future knee operation.

Figure 10:
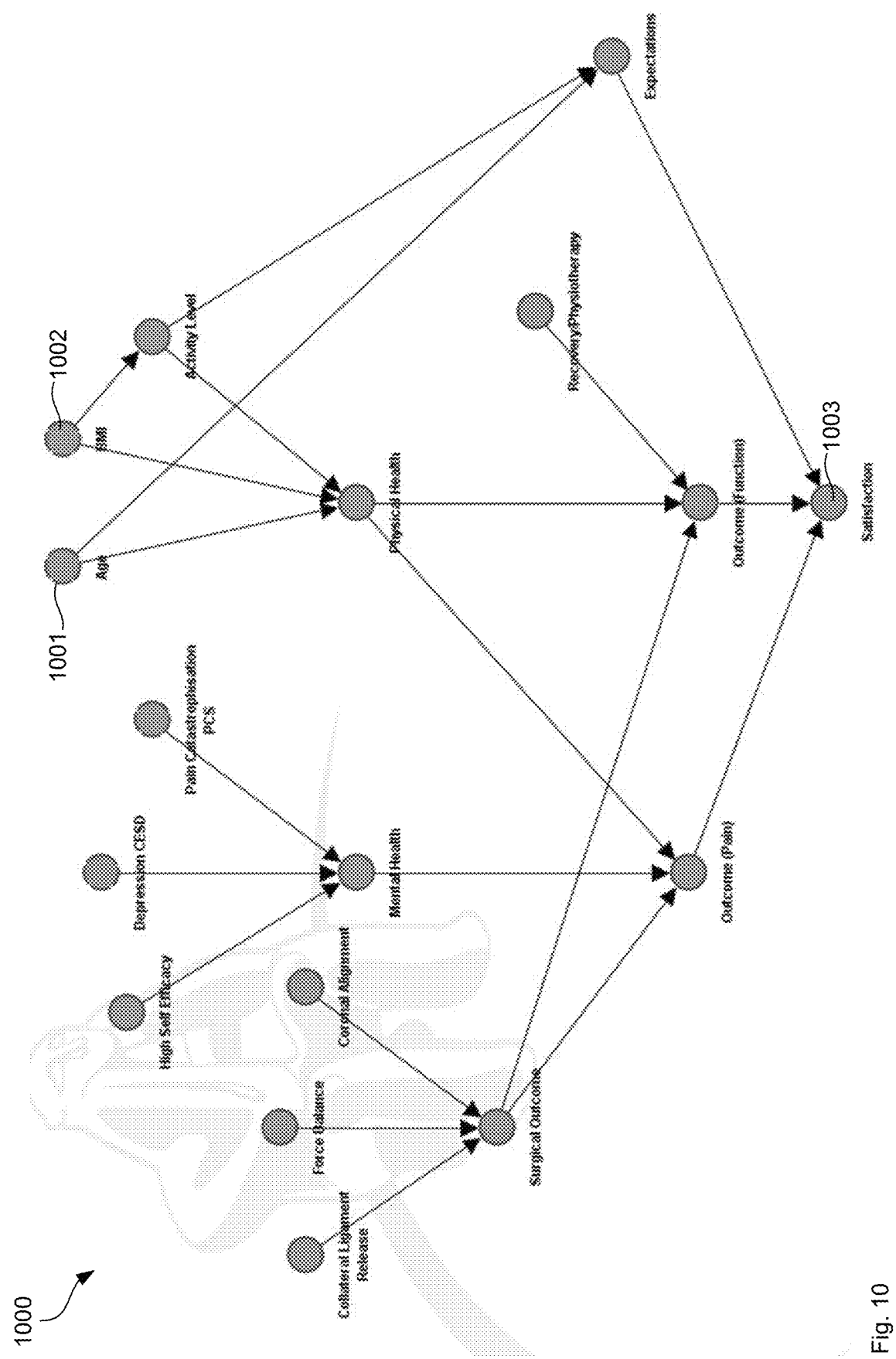
FIG. 10 illustrates a statistical model as stored on data memory.

FIG. 10 illustrates a statistical model 1000 as stored on data memory 106. The statistical model 1000 comprises nodes represented by discs and edges represented by arrows. The nodes are stored on data memory 106 and represent the patient input data, such as age node 1001 and BMI node 1002 and the predicted satisfaction value at output node 1003 that represents the output of the machine learning model as described in method 200. The nodes are stored an data memory 106 as a data structure, such as a list where new nodes are appended for example node_list.append(new Node("Age")) for creating the age node 1001. In this example, the label "Age" is unique such that the age node 401 can be retrieved by searching for this label node_list-.find("Age"), which returns a pointer to a Node object.

Similarly, the edges are also stored on data memory 106. The edges between the nodes represent conditional dependencies between the patient input data and the predicted satisfaction value. Edges are appended to a global edge list by edge_list.append(new Edge(node_list.find("Age"), node_list.find("Satisfaction"))) to create a direct edge between the age node 1001 and the satisfaction node 1003.

In one example, the statistical model 1000 is a Bayesian network, that is, a directed acyclic graph (DAG). In this example, the nodes represent random variables in the Bayesian sense: they may be observable quantities, latent variables, unknown parameters or hypotheses. Edges represent conditional dependencies; nodes that are not connected represent variables that are conditionally independent of each other.

Each node is associated with a probability function that takes, as input, a particular set of values for the node's parent variables, and gives (as output) the probability (or probability distribution, if applicable) of the variable represented by the node. For example, if m parent nodes represent m Boolean variables then the probability function could be represented by a table of $2^m$ entries, one entry for each of the $2^m$ possible combinations of its parents being true or false.

For example, there may be multiple age related nodes where each node is indicative of whether or not the patient age is within a predefined age bracket. Such as a true or false value for the statement "age is below 40". Other representations could include multiple sub-tables for groups of parent nodes with dependence upon each other. The edge weights may be considered machine learning model parameters.

In other examples, statistical model 1000 is an undirected, and possibly cyclic, graph; such as a Markov network.

The satisfaction node 1003 may also be a Boolean node representing whether or not the patient is satisfied with the operation. This way, the probabilities given the actual patient input data as described above can be propagated through the statistical model 1000 to calculate a final probability for the patient being satisfied, that is, a probability for a value of '1' or 'True' at the final satisfaction node 1003. This probability can then serve as the predicted satisfaction value. An example of this is that a BMI over 40 and age under 55 years would return a predicted satisfaction value of '64%', indicating that there is a 64% chance of the patient being satisfied after the operation, and that the relatively young age and high BMI has negatively impacted her chance for a successful outcome.

The example of FIG. 10 is a hierarchical model, which means that there is at least one path from the patient input data to the predicted satisfaction value 1003 having at least two edges. For example, the path from age node 1001 to satisfaction node 1003 contains four nodes in total and three edges between them.

Finally, processor 102 generates an electronic document comprising a surgeon report associated with the future knee operation to indicate to the surgeon the predicted satisfaction value.

In one example, processor 102 determines a statistical transformation of the predicted satisfaction value before generating the report, such as scaling the predicted satisfaction value to patient distributions of answers, such as the distribution of answers of other patients of the same doctor.

In further examples, the distribution of answers is drawn from one or more of:
  postoperative outcome,
  preoperative baseline,
  healthy patient baseline,
  postoperative high achievers, and
  postoperative low achievers.

Processor 102 may further perform the statistical transformation by performing a conversion to odds ratio or risk factors.

Processor 102 may generate the surgeon report by generating a graphical depiction of one or more of:
  boxes,
  vertical bars,
  horizontal bars,
  graphical elements with a colour scale mapped visual output,
  conversion to percentages,
  embedding into customizable lines of text, and
  specific highlighted risk factors indicated to patients.

Figure 11:
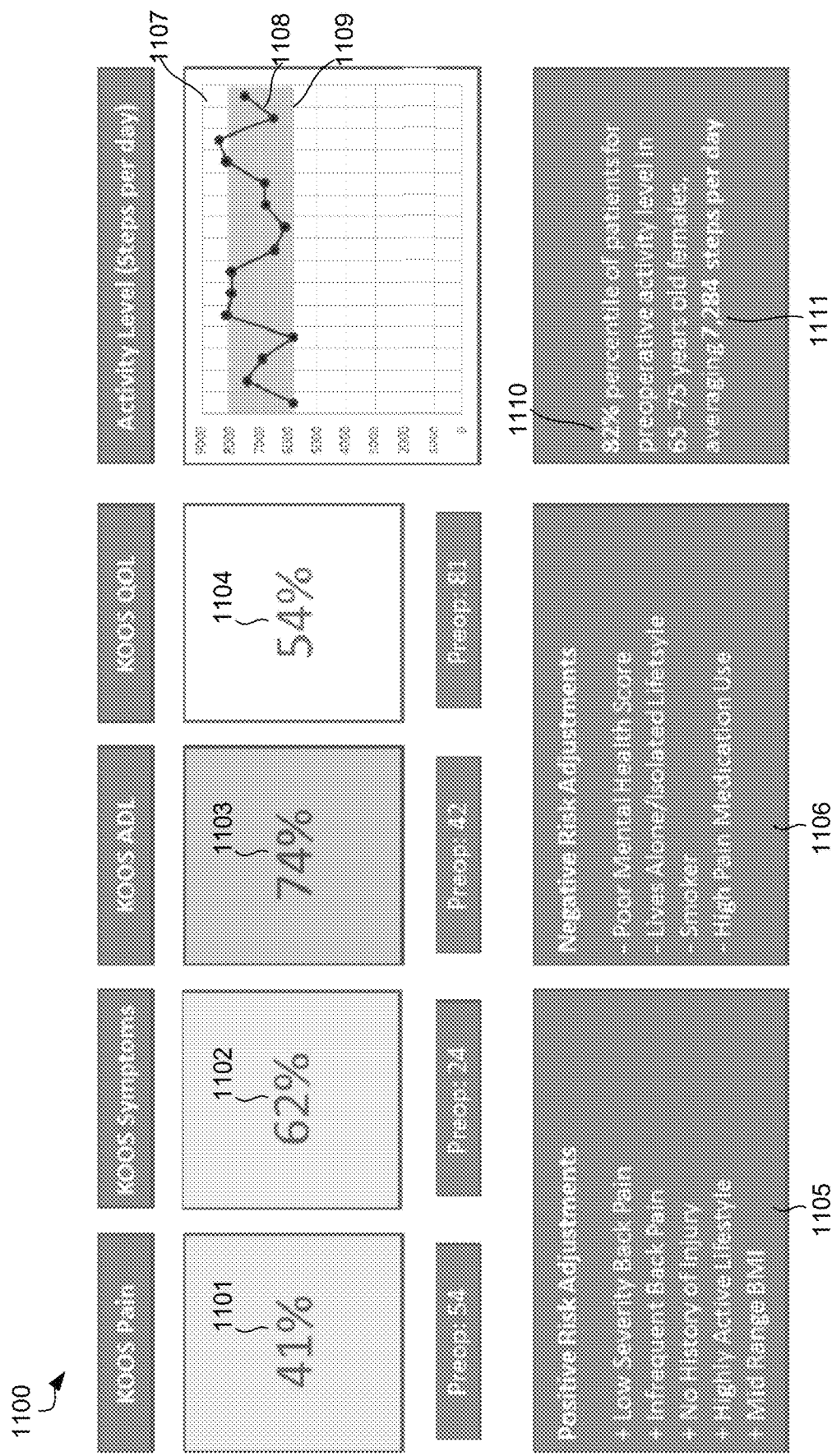
FIG. 11 illustrates an example surgeon report.

FIG. 11 illustrates an example surgeon report 1100. In this example, the statistical model 400 has multiple outputs. That is, processor 102 determines multiple predicted satisfaction values, which may be considered influencing factors of a final satisfaction value. In this example, processor 102 determines partial satisfaction values/influencing factors from the Knee injury and Osteoarthritis Outcome Score (KOOS) In particular, processor 102 determines a predicted pain value 1101, a predicted symptoms value 1102, a predicted function in daily living (ADL) value 1103 and a predicted knee related quality of life (QOL) value 1104.

Surgeon report 1100 may further comprise a first indication 1105 of patient input data, that is, answers selected by the patient, or summaries of those answers that affect the risk positively. This means these answers lead to a higher probability of patient satisfaction. For example, the patient answers that he has low severity and infrequent back pain. This makes him more likely to be satisfied with the knee operation than other patients with high severity and frequent back pains.

Similarly, report 1100 comprises a second indication 1106 of negative risk adjustments, such as poor mental health score, isolated lifestyle, smoker or high pain medication use.

Processor 102 determines the positive risk adjustments 1105 and the negative risk adjustments 1106 by selecting the patient input data that has a contributing value that is less than the final value. In other words, processor 102 compares the probability of the path from one patient input node to the output node to the final predicted value. If the edge probability is less than the final value, processor 102 selects that patient input node as a negative risk adjustment and vice versa for edge probabilities that are higher that the predicted value. Processor 102 determines the positive risk adjustments 1105 and the negative risk adjustments 1106 by selecting the patient input data that has been previously identified as having a positive or negative relationship with the perceived satisfaction value, in the context of other conditionally dependant inputs. These relationships could be predetermined and stored in a data table in data store 106 along with the appropriate text string to display.

Report 1100 further comprises an indication of an activity level of the patient. In the example of FIG. 5 this indication is a chart with the number of steps displayed for each day before the surgery or consultation as a line 1108. The chart 1107 further comprises an indication of the variation 1109 of the number of steps, which in this example comprises two horizontal lines to indicate a performance band for the patient, colour coded to indicate the activity level the patient is achieving relative to gender & BMI adjusted norms.

Report 1100 further comprises an indication of the percentile 1110 of the activity level of this patient within patients in this age group and gender and an average value 1111.

Figure 12:
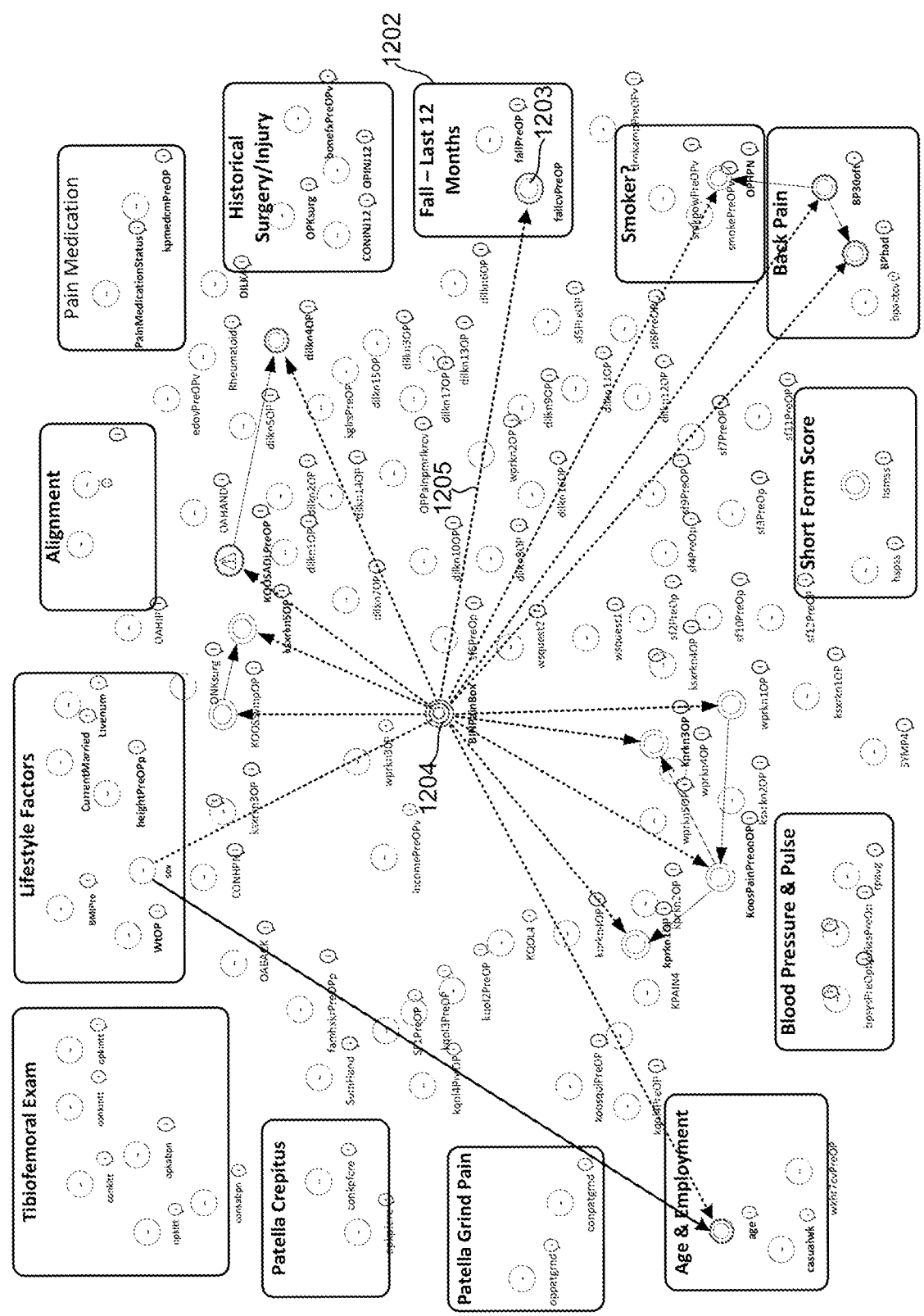
FIG. 12 illustrates another example of the statistical model.

FIG. 12 illustrates another example of the statistical model 1200. This example is a data fed, supervised learnt model in order for processor 102 to calculate a prediction of a central node (in this case, postoperative self-reported pain). The nodes are binary, which means questions that are answered in the positive or other patient data that meets a predetermined criteria is illustrated as bold and connected. Each set of linked nodes defines a conditional probability table.

For example, in the fall group 1202, the patient has answered that he had a fall in the last 12 months and therefore, the corresponding fall node 1203 is illustrated in bold. The fall node 1203 is connected to pain node 1204 by edge 1205 indicating that the fall in the last 12 months makes satisfaction with the level of post-operative pain less likely.

Figure 13:
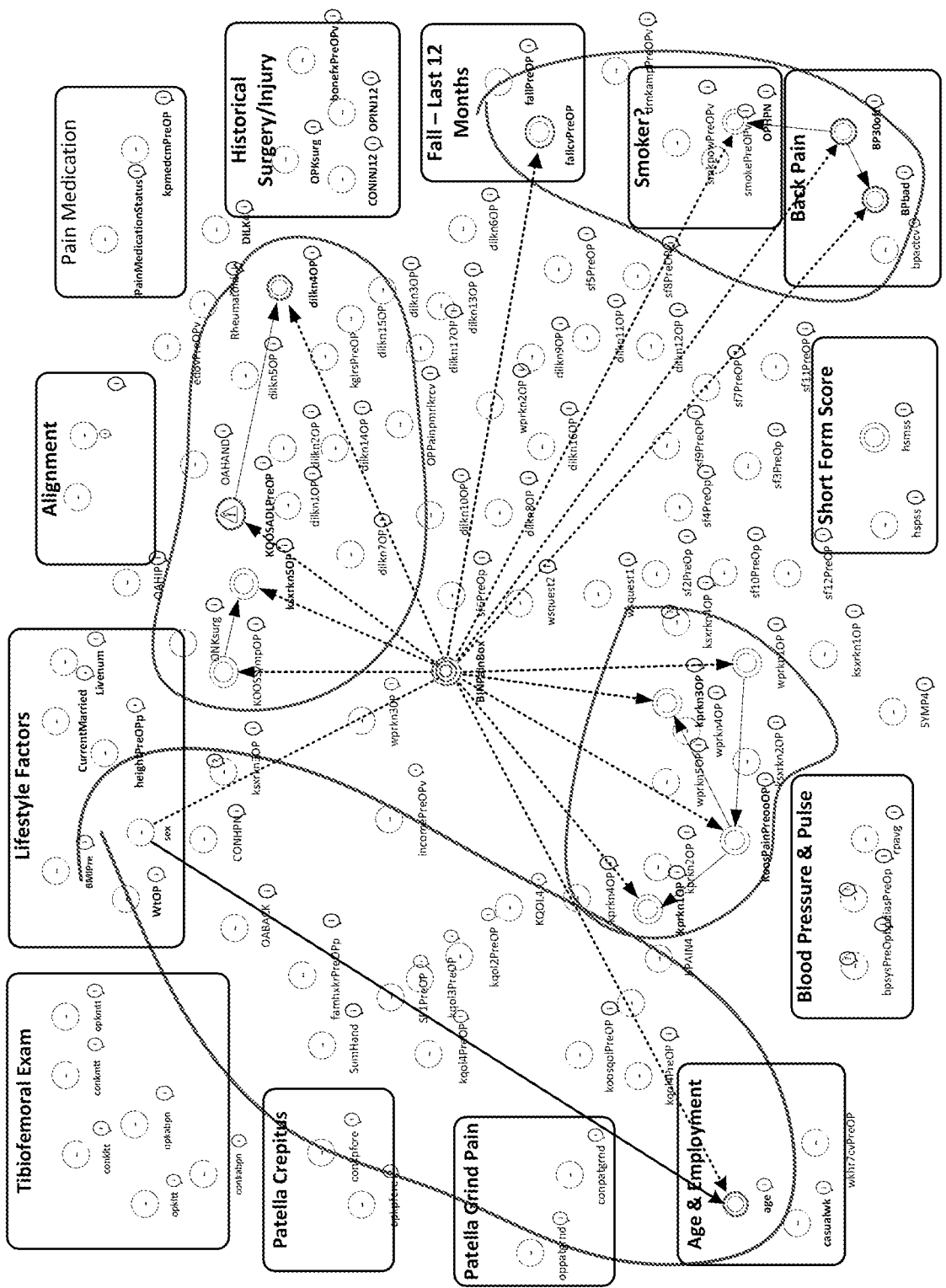
FIG. 13 illustrates the statistical model from FIG. 12 in more detail.

FIG. 13 illustrates the statistical model 1200 from FIG. 12 in more detail. This may be the back end structure for pulling the prediction once learnt. Each circle in FIG. 13, such as circle 1302 represents an independent Markov blanket ∂A of factors that processor 102 can fully define in a lookup table with little lag. The Markov blanket of a node contains all the variables that shield the node from the rest of the network.

This means that the Markov blanket of a node is the only knowledge needed to predict the behaviour of that node.

An example of a calculation incorporating the lookup table structure defined in FIG. 13 would include the following: a prior probability for likelihood of satisfaction (80%), the patients age (64), gender ("Female"), current KOOS pain, symptoms & ADL score (38, 51 & 62) in the affected knee, specific answers to KOOS pain subsection question 2, 5 & 8 ("Mild", "Moderate" & "Severe"), falls in the last year (2), reported severity & frequency of back pain ("Severe" & "Daily") and presence of pain in the hip of the affected knee ("Yes"). For the calculation, processor 102 retrieves the lookup table of expected value based off the age and gender, KOOS pain results, other KOOS results & back pain, hip pain and number of fall results. These values are 84%, 72%, 77% & 47%. The equation may be as follows where n is the number of lookup tables used:

$$\frac{\sum\limits_{n}^{i=1} ExpectedValue_n (1-prior)^{n-1}}{\sum\limits_{n}^{i=1} ExpectedValue_n (1-prior)^{n-1} + \sum\limits_{n}^{i=1} (1-ExpectedValue_n) prior^{n-1}}$$

Here this resolves to:

$$\frac{(84 \cdot 72 \cdot 77 \cdot 47) \cdot (20)^3}{(84 \cdot 72 \cdot 77 \cdot 47) \cdot (20)^3 \cdot (16 \cdot 28 \cdot 23 \cdot 53) \times (80)^3}$$

or a predicted satisfaction chance of 38.51%.

In a Bayesian network, the values of the parents and children of a node evidently give information about that node; however, its children's parents are also included, because they can be used to explain away the node in question. In a Markov random field, the Markov blanket for a node is simply its adjacent nodes.

Processor 102 can then calculate the joint probability from each table result by Pr(A|∂A, B)=Pr(A|∂A) where the blanket ∂A is the set of nodes composed of A's parents, its children and its children's other parents. This approach facilitates the processing of practically sized data sets.

The application front ends (patient & surgeon) as well as the web service may be implemented in C++. The database to store the nodes and edges and other data may be MySQL. A single database both holds the tables of predictive values to look up and patient records of the patient and their answer set. Processor 102 may execute a software called BayesiaLab by Bayesia S.A.S. for the predictive modelling.

Figure 14:
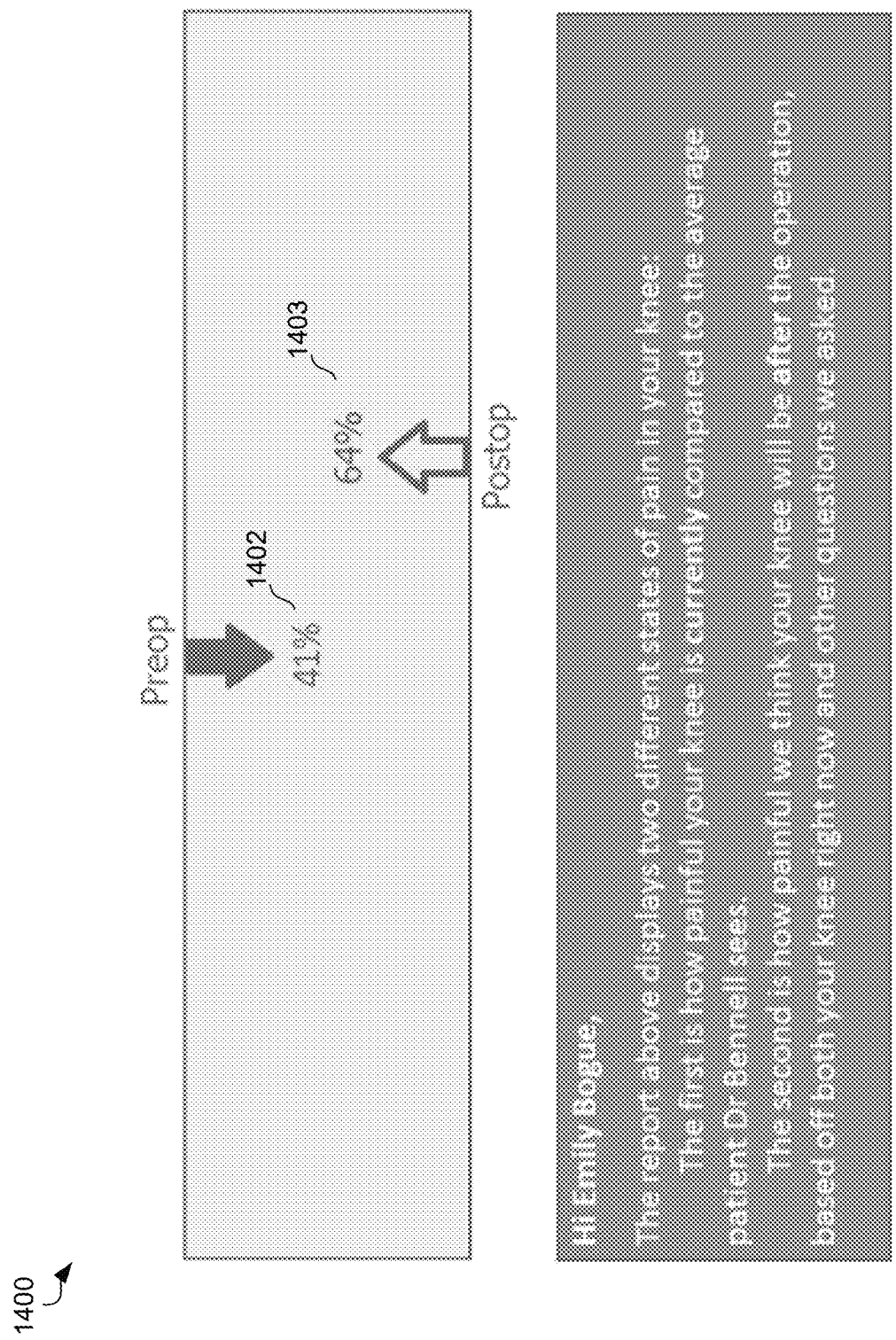
FIG. 14 illustrates another example of a report.

FIG. 14 illustrates another example of a report 1400. Report 1400 interprets predicted satisfaction value as pain in order to reference the preoperative state against the postoperative. Report 1400 comprises a pre-operative pain value 1402. This value has been determined from placing the patients preoperative self reported pain level against the distribution of patients who've come into the surgeon's rooms. This is expressed as a percentile rank. In addition, report 1400 comprises a post-operative predicted pain value 1403. Processor 102 determines the post-operative value 1403 by receiving patient input data before the operation as described above. This data is then used to place the patient against the same distribution in order to draw a predicted postoperative percentile rank Report 1400 showed that the predicted percentile increases from 41% to 64% as a result of the operation. Report 1400 also contains a brief explanation of the meaning of the other elements of the report.

Figure 15:
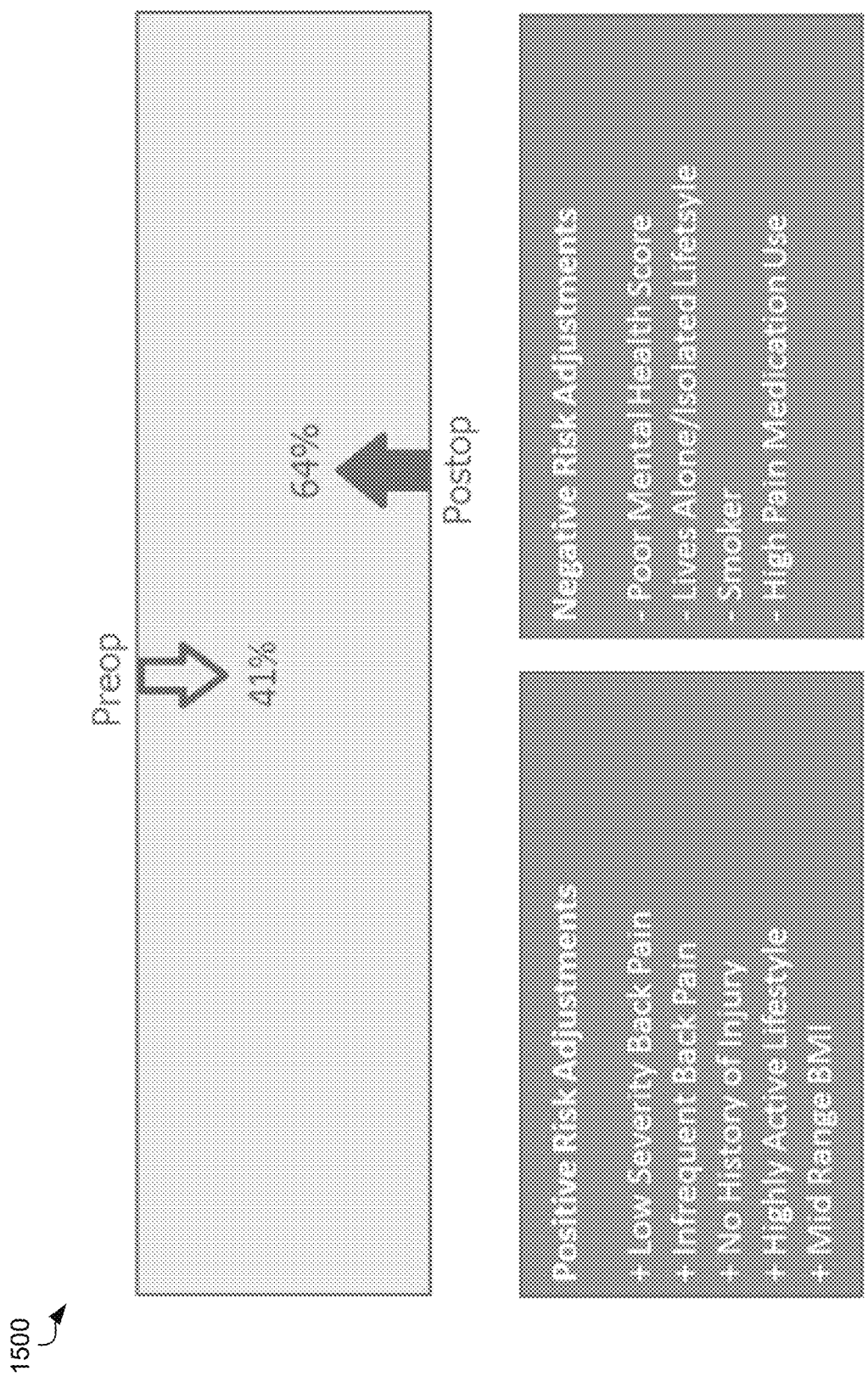
FIG. 15 illustrates the result of an interactive element in the report.

FIG. 15 illustrates report 1500, the result of an interactive element in report 1400. Here the postoperative indicator arrow has the functionality of a button, changing the bar to a postoperative mode which has triggered an animated colour change in the percentile bar. Also triggered is the generation of an indication of positive risk adjustments and negative risk adjustments similar to the report in FIG. 11.

Referring back to FIG. 11, it is noted that in one example, the individual elements of the report may be customised or selected to be shown or not shown. In other words, the prediction front end is created in a modular manner to allow surgeon customization of what is shown and how it is shown.

Figure 16:
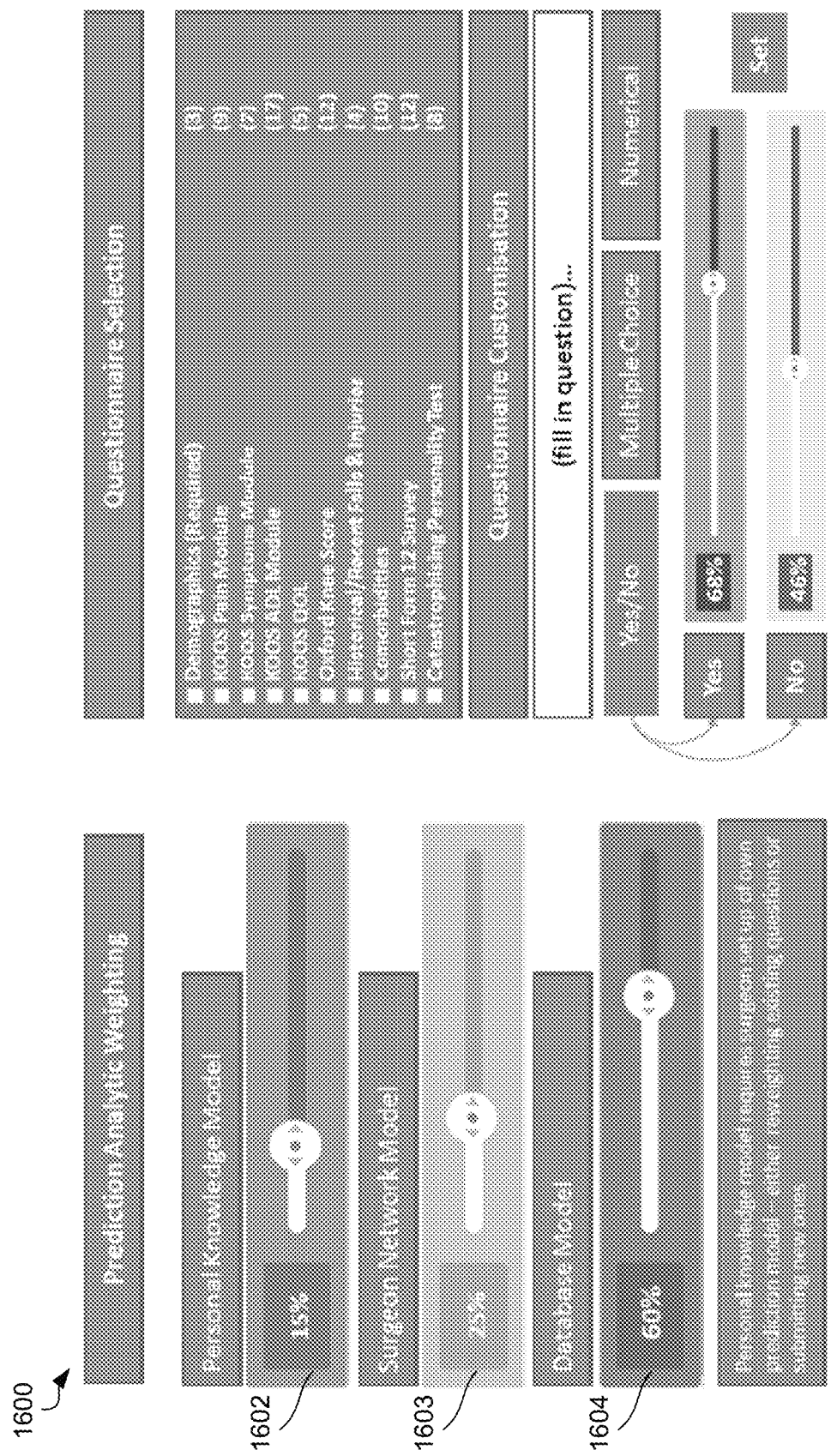
FIG. 16 illustrates an example of a 'settings' back page.

FIG. 16 illustrates an example of a 'settings' back page 1600 allowing some customization of model weightings. The model weightings are broken into 3 groups—collective expert knowledge model 1602, individual surgeons' expert model 1603 and the data base model 1604. A user can adjust the weights by moving the respective slider and can adjust the 'yes' and 'no' weights for each of the questions from the questionnaire separately.

In other words, processor 102 generates the expert user interface 1600 comprising the expert data input 1602 to 1604 for expert input data indicative of the conditional dependencies between the patient input data and the predicted satisfaction value. Processor 102 receives the expert input data and determines the conditional dependencies between the patient input data and the predicted satisfaction value based on the expert input data. Finally, processor 102 stores the conditional dependencies as part of the statistical model on a data store 106 such that the conditional dependencies are based on expert network modelling and expert opinion as reflected by the expert input data. It is noted that the expert may be a surgeon, a patient, a nurse, a physiotherapist, a psychologist, or an allied health professional.

Figure 17:
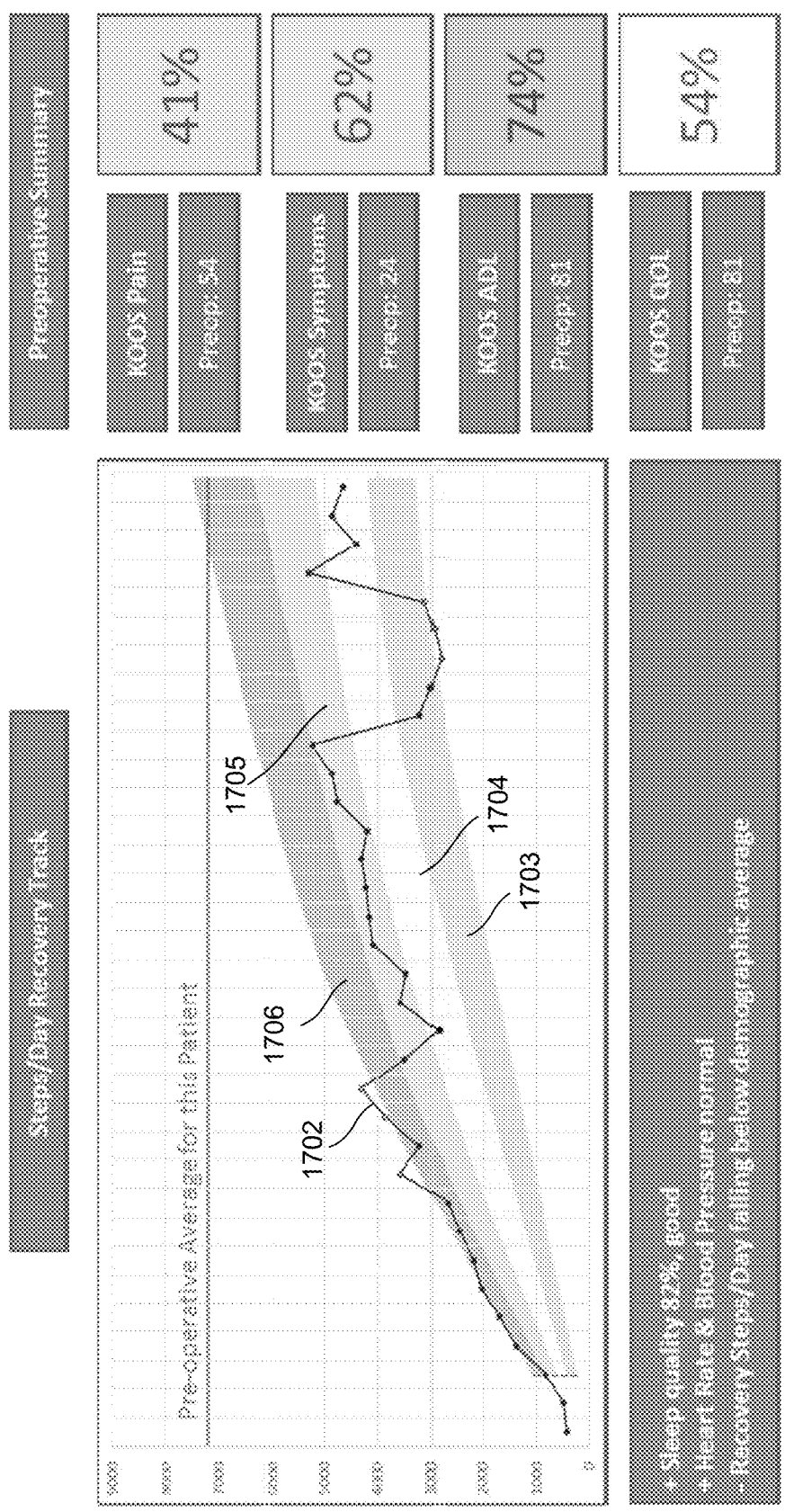
FIG. 17 illustrates a postoperative monitoring user interface.

FIG. 17 illustrates a postoperative monitoring user interface 1700 for reporting step count of a patient 1702 against normalized expected recovery curves for very low 1703, low 1704, normal 1705 and high 1706 step counts. Additional data could be integrated into this postoperative monitoring interface such as sleep quality, heart rate & blood pressure. These could be displayed either textually as illustrated in FIG. 17 or via a custom display.

In one example, processor 102 further receives intra-operative data and post-operative data, such as through an additional user interface. For example, the deviation from the cut angle or any other inter-operative adjustments can be entered into the system 100 and after the knee operation processor 102 can then determine a revised predicted satisfaction value based on the intra-operative data and the post-operative data. The post-operative data may also be post-operative patient input data provided in a questionnaire.

Processor 102 may further determine a cost of an error as measured in terms of patient outcomes and may determine future outcome gains or losses. Processor 102 can then determine subsequent treatment decisions based on the future outcome gains or losses.

In some examples, the surgeon report comprises an indication of one or more of
generic/holistic measures of health,
specific functional attainments,
postoperative range of motion,
postoperative time to mobilisation, ambulation,
activity level, and
risk of adverse events.

Processor 102 may further perform a kinematic simulation of the knee joint, such as based on a mechanical model of the knee characterised by computer tomographic imagery. The simulation simulates the result of reconstruction of the total knee replacement. Processor 102 receives the kinematic simulation data from the simulator, such as by retrieving the simulation data from data store 106. The patient input data is indicative of activity desires or patient behaviour, and the nodes of statistical model comprise nodes representing the kinematic simulation data and the patient input data indicative of activity desires or patient behaviour.

For example, processor 102 may simulate the varus/valgus value of the knee, which can then become one of the nodes of the statistical model. The statistical model may further comprise nodes for activities, such as playing golf. A particular varus/values value may make playing golf more painful and therefore lead to a lower predicted satisfaction value, for example.

The methods described herein may also be used for operating a healthcare system. In particular, processor 102 may perform the method 200 in FIG. 2 to determine a predicted satisfaction value for each of multiple patients enrolled in the healthcare system. Processor 102 may then determine a patient care item for each of the multiple patients by maximising utility of healthcare spent in the healthcare system. For example, processor 102 may determine whether the cost for additional physiotherapy treatment outweighs the expected gain in predicted satisfaction value.

By combining the multiple patients at the same time, processor 102 can minimise the global overall cost with a collective satisfaction or patient outcome target and perform a per patient cost minimisation with a per patient satisfaction or patient outcome target. Processor 102 may also perform fixed global cost allocation with a satisfaction or patient outcome target maximisation.

Maximising utility may be based on a predetermined amount of cost expenditure for each of the multiple patients. For example, processor 102 may receive an indication that $10,000 can be spent on each patient and determines the optimal allocation of that amount in order to achieve the maximum predicted satisfaction value.

At the core of the issue of bias is a definitional difference between the surgeon and the patient's definition of what constitutes a successful surgery, and the failure to fully align patient expectations with the reality of their likely surgical outcome. One mechanism of eliciting a patient's measured outcomes is through the use of Patient Reported Outcomes Measures (PROMS).

A range of scoring metrics may be used which aim to strike different balances between incorporating objective, directly measurable data such as range of motion (ROM) measurements and subjective, questionnaire based data in order to elucidate and characterize patient dissatisfaction in a way that makes intervention feasible.

The advantages of the former are its reproducibility; however, the clinical relevance suffers in comparison to direct patient reported results. Another approach involves high levels of complexity in patient outcome questionnaires such that each question focuses on a very specific scenario or source of pain or dissatisfaction; however, this comes at the cost of exposure to survey fatigue or a reduction in the clinical practicality of administering the questionnaire. Further developments include attempts to resolve the clinical burden through an adaptive questionnaire format in order to get specific information that characterizes a patient's expectations and aspirations. While this approach is highly relevant to the aim of providing personalised medical care, it does lead to potential issues around database completeness for data analysis and patient outcome prediction work.

Examples of patient focused scores are the Knee Osteoarthritis & Injury Outcome Score (KOOS), the Oxford Knee Score (OKS) and the Western Ontario and McMaster Osteoarthritis index (WOMAC).

More general questionnaires include the SF-36, used in conjunction with a specific knee functional questionnaire. The final structure of scoring for TKA outcome looks directly at the satisfaction level of the patient, either by directly asking if they're satisfied with the surgical outcome, using a visual analog scale construct or generating a Patient Acceptable Symptom State (PASS) for an existing scoring structure to binarise the patient groups into either satisfied or unsatisfied groups.

Alignment of implant components to the bone may be a benchmark for measuring short term outcomes in Total Knee Replacement, and this may correlate with survivorship. This reduces the knee replacement operation to one in which a simple mechanical optimization is all that is required to achieve a 'success', which may not equate to a satisfied patient. A variety of other factors, some surgical and some patient linked, may drive outcome.

Risk factor analysis for Total Knee Replacement is one example, which may target one of two primary goals—either a risk factor identification approach (where the focus is on identifying singular key factors that are indicative of a major complication being probable) or outcome prediction (where the consideration is wider with regards to interdependency of input variables, at the cost of presenting a singular focus or isolating an intervention's impacts as accurately as possible). The endpoints targeted may be incidence of reoperation, length of stay greater than four days, readmission within one month and postoperative complications (orthopaedic and non-orthopaedic). A major advantage may arise if the data covers a single joint centre with a fairly large database of patient results. This controls for a number of variables that mixed-source datasets suffer from as confounding variables. On the other hand, the scope of the endpoints may be somewhat limiting, relying entirely on hospital based-admissions data and not (typically noisier, but more long term clinically relevant) PROMS measures. The statistical procedure of analysis, stepwise multivariate regression (with some filtering of inputs based off logistic univariate regression statistical significance) is one approach to risk analysis.

The data may comprise some noise by considering length of stay as a factor, and the endpoints are generally constructed around managing the cost of care in the short-medium term, likely capturing risk factors relating to infection or patients predisposed to present as dissatisfied regardless of the actual surgical outcomes. Psychiatric comorbidities present as the greatest single source predictor of negative outcomes for all endpoints considered. This, although not based off PROMS analysis, is useful in that it underscores even when considering for endpoints best designed to capture the impact of variables directly related to operative issues in surgery, the dominant factor in patient outcome is the presence of a psychiatric comorbidity—a factor related dominantly to the patient, rather than the surgery. This reasoning does not consider the likely causal contribution of a worse case of knee osteoarthritis acting as a contributing factor to a patient's psychiatric comorbidity risk, however, and it is worth noting that the input variables do not contain any radiographic or other preoperative osteoarthritic state variables.

Predicting patient reported outcome measures may be devised around the WOMAC score as both a preoperative input and a target prediction. The Short Form 36 Questionnaire (SF-36) may be used, as a validated, more general patient response centered health measure as an additional preoperative input to the standard demographic factors and socioeconomic factors. This approach may suffer somewhat from the issue outlined above if it considers patients recruited from joint centers in Australia, the United Kingdom and the United States. Each of these markets have fundamentally different healthcare regimes that affect a patient's surgical experience and characterise the demographics for the relevant patient groups selected (that is, it is not just the patient's experience in receiving a joint replacement but who was able to receive a joint replacement in each country.)

Although it may be possible to control for this as a factor, several distortions exist such as the US centers treating a much higher percentage of high income and high education patients. While the aims are to identify factors that survive these differences in order to characterise robust preoperative predictors, the presence of a limited but disparate sample of patients does not guarantee identified factors will be relevant to the population as a whole.

Some control may be achieved, however, by pursuing a hierarchical model rather than a regression based analysis, limiting the vulnerability of a regression model that may map itself to a non-linear population function that is only presenting some part of its structure with the selective sampling. In one example, the greatest single determinant of postoperative outcome in WOMAC's function and pain scores is the preoperative result for those same scores. This presents a question in terms of what it is capturing—do patients suffering from osteoarthritis to a greater degree prior to their operation have a worse outcome after surgery, or is it simply that patients who innately perceive their state to be worse continue to do so after surgery? The question begins to border on philosophy when considering the intent of the relevant PROMS scores (is it to present an objective as possible measure of a result that is only considered subjectively or is it to embrace the subjectivity of the patient's experience of their condition?) but does have relevance in the context of whether the better figure to consider from a machine learning perspective is the amount of patient improvement or their final state. Further, the SF-36's mental health subscore may be another key predictor presenting some support to the idea that patient perception is a factor, likely one which has seen some of its weight in this model absorbed in the preoperative WOMAC variables due to the inherent greater correlation the preoperative and postoperative scores are likely to have to each other than the results of another measurement instrument, even if the preoperative score is reflecting a correlative bias with the mental health score (the postoperative score being a strong correlation).

On a whole, this example underscores the tangled webs of causality that emerge when applying frequentist statistics methodology to a machine learning problem as complex as this. The impact of psychological distress may characterise some of the mental health score as a reversible issue following surgical intervention, though to what extent the causal link is the preoperative patient's knee state driving their low mental health score may be captured by radiographic or other osteoarthritis score based variables.

The interplay of measured factors as indicators of patient satisfaction and their interplay with geography and hence the relative sampling of those patients may be relevant. The EQ5D depression score may be considered in addition to the IMD—Index of Multiple Deprivation, an Oxford University score of the socioeconomic deprivation of an area measured across indices of income, employment, health deprivation and disability, education, skills and training, barriers to housing and services, crime and living environment.

The IMD may be a significant predictor. It does not seem that where a patient lives alone is sufficient to drive their TKR outcome as there is no credible causative link. The causative links that can be identified are a) a poorer quality of healthcare provided to those with a lower means, though the publicly managed nature of the healthcare systems suggests this isn't the key driver (notwithstanding some potential self selection of higher experience surgeons to more 'prestigious' hospital environments which could receive a patient group from an, on average, less deprived geographic locale), and b) a somewhat reduced 'drive' or other mental characteristic relating to patient rehabilitation conformance and outcome perception. The need to identify the driving factors in a set of predictors is less pronounced when considering a single predictive model in isolation, but if attempting to combine insights from models with separate controls and co-predictors it becomes an important tool in identifying what predictors being introduced are presenting unique, uncross correlated information in the absence of a full dataset to test this.

Mental traits that render a patient more or less susceptible to a poor postoperative outcome may also be characterised. A regression analysis relationship may be found between the WOMAC pain and functional score outcomes and the psychological attribute self efficacy, a measure of "the conviction that one can successfully execute the behavior required to produce the outcomes", in this case, of a successful TKR operation recovery. This can then be thought of as a derived attribute, in that it captures both the patient's assessment of their own willpower as balanced against their perception of the relative difficulty of the road to recovery. It may also capture some hidden correlations not captured in the variables, as the measure is likely to correlate with the delay the patient has allowed themselves to undergo before seeking treatment, and hence the severity of osteoarthritis at surgery.

Self-efficacy may be an independent predictor of patient outcome. As such, other mental attributes may be incorporated into the regression analysis, many of which have very high correlations and hence lead to some results vulnerable to misinterpretation. One such result is the high level of power given to anxiety to predict poor pain outcomes in the multivariate analysis, which is likely reflecting a combination of its correlation with depression and depressions own negative correlation with pain severity and the ceiling effect of the score. As such, it is important in regression based models to interpret the true independence of a predictor through the lens of what other factors it has been regressed with, while also understanding the many layers of abstraction that separate what is actually being assessed. At its core, in preoperative prediction it is the patient's psyche and its impacts on their response to their changing pain state that is under review, and the underlying factors that contribute to their response to surgery are no doubt imperfectly captured by static instruments tuned to measure rigidly defined psychological attributes.

Nevertheless, self efficacy is a useful factor to incorporate in that it captures psychological information explicitly linked to the patients osteoarthritic state and upcoming surgery (it is a measure of how capable they feel of overcoming specific challenges), something which more generic mental health scores do not touch upon. As such, studies are still able to identify self efficacy as a significant predictor of functional outcome, though not pain.

The causal link might be that greater pain is not in anyway mitigated by self efficacy, but the pain aversion based component of a patient's functional outcomes are—more self efficacious patients are better equipped to overcome pain in restoring their lifestyle. As an observation from this, it is worth keeping in mind the nature of PROMS scores in that their construction and categorization into subscores such as pain and function is not an attempt to isolate specific components of a patients experience post surgery, but to form a number of (sometimes subtly) different clinical perspectives with which to assess their outcomes. It is therefore interesting that the regression may not choose to use preoperative pain as a regressor for postoperative functional outcome or vice versa. It is reasonable to hypothesize that if self efficacy is capturing the capability of a patient to overcome pain-based disability postoperatively, then a patient with a much higher preoperative functional state than their pain state is one who is highly self efficacious and the addition of the additional score required to assess this pre-clinically is redundant. Relationships such as this, where existing clinical tools may partially capture elements of a relevant underlying factor isolatable in a separate instrument are precisely the application in which a machine learning rather than a linear regression based approach could advance the field of postoperative outcome prediction significantly.

Some further evidence exists that self efficacy is a major factor. A similar study assessing personality type with a validated instrument as a predictor of TKR showed personality types identified as 'unstable introverts' as being the least likely to express satisfaction post surgery. There may be a correlation of this personality typing with self efficacy and pain catastrophising behaviors, and the personality tests showing metrics of neuroticism and extraversion are presented as alternate categorical labels for tendency to catastrophise and self efficacy. Personality subtyping may be independent from self efficacy or other factors but instead some examples profile another instrument with a more discrete categorisation, acknowledging the problem of an enormous amount of psychological attributes, all of which are imperfectly captured by questionnaire instruments both in terms of design and in terms of response noise and even if they were captured perfectly with regards to their definitions, represent factors that are highly correlated.

As such, making decisions on which of these instruments are to be utilized requires considering multiple dimensions, with a limit to those to be included expressed in terms of the increasing noise in results as a result of survey fatigue and clinical practicality issues. The amount of correlation or predictive power contributed difficult to assess.

There may be an ability to separate several mental constructs such as optimism, pessimism, hope, treatment credibility and treatment expectancy into their constituent constructs be identified as independent factors and show that, despite enormous cross correlations, the individual psychological factors can be uniquely separated. However, incorporating a general factor into a five factor model may identify a better fit to the data, despite the presence of some specific variance, suggesting the clinical relevance of separating these unique mental constructs may be limited.

Another metric is called the Injustice Experiences Questionnaire (IEQ), adapted for TKR recipients. The questionnaire may cover three major aspects—do the patients consider their condition irreparable or believe that their life has been permanently negatively impacted, do they interpret it as being in some manner "unfair" and do they consider someone else partly at fault for their condition. One example is a stepped introduction of factors into a linear regression model, assuming they factor their wish to correlate has the least significance and is introduced last, aiming to predict WOMAC pain and function scores. Dominant factors may be presurgical pain and function scores, and it is worth keeping in mind that these scores may drown some of the significance of other psychological scores (as a patient's measure of their pain right now can be assumed to capture some level of the psychological factors dictating their likely pain response in the future.)

However, when analysed in univariate regressions, the IEQ may have a stronger correlation. It is worth considering the nature of the IEQ and the postoperative scores being considered here, however. The results for the IEQ questionnaire may be lower (by a factor of 2 to 3) to scores recorded in the questionnaires native domain of injuries and accidents. The patient group may be older and may be suffering from a degenerative condition without a salient source to direct their blame towards. As such, it is possible that the IEQ is acting as a filter for a relatively small amount of doomed-to-dissatisfaction patients, rather than a tool capable of categorizing patients across the breadth of outcomes.

This would lead to it identifying as a statistically powerful tool for regression as its numerical distribution of results (many low scores with a long tail of higher scores) is biased in a manner predisposed to fit with the ceiling effect and long tale of post-operative outcomes scores. It follows then that a relatively small number of very accurate predictions could be fueling a strongly reported fit. This is another application where a machine learning algorithm (even one as simple as a CART analysis) might produce more meaningful observations.

TKR satisfaction may be considered from the perspective of categorizing who is satisfied and who is not without a focus on prediction by allowing other postoperative variables to feed into the patient's prediction of satisfaction. The greatest 'predictor' of dissatisfaction may be when the patients expectations have not been met, more so than any other preoperative or postoperative factor.

The lens of a patient's presurgical expectations might be an effective way of 'gating' the many preoperative psychological attributes that may impact on outcomes into a single factor Patient expectations, as a major predictor, represent a very realistic pathway for future interventions towards improving patient outcomes by aligning patient expectations to their surgeons.

Overly optimistic patients who do not achieve their unrealistic expectations have a believable path to poor performance as a result of their mindset; similarly, overly pessimistic patients may be dooming themselves to a negative perception regardless of their actual surgical outcome. On another note, the ability to predict with some confidence a patient's outcome, and present it to them as slightly more optimistic than it actually is may push the patient towards better outcomes, ethical considerations notwithstanding.

Possible mechanisms to drive surgeon-patient expectation alignment begin with first measuring the expectation gap between surgeons and patients on a per patient level using a validated questionnaire instrument. This may comprise patient education classes or other information dispersion mechanisms to effect their impact on patient's preoperative expectations. Some examples use personalized reports or information in their educational structure. As such, they have necessarily incorporated an understanding of the patient decision making process into their design & development and an understanding of the psychosocial factors at work. By incorporating risk factors identified from a patient prior to their operation into a decision support tool for the patient with personalized risk factor evaluations, this gulf could potentially be bridged.

One example is looking at presurgical expectations and breaking it down into response expectancies and behavioral outcome expectancies. Response expectancies cover involuntary factors such as pain and ability to sleep. Behavioral outcome expectancies cover factors related to the patient's own decision making such as their capability to overcome specific barriers. The two factors are linked in a similar way to how self efficacy is linked to preoperative pain scores, but capture both factors in the context of the patients expectations preoperatively about the post-operative state. The results show that the behavioural outcome expectancies better predict pain severity and function at follow up than response expectancies do and outperforms other psychological attributes outside of pain catastrophising, lending further credence to the idea that incorporating some element of a patient's beliefs about their own capability tempers the noise found in purely psychological attribute based predictions.

Pain catastrophisation, as a potential predictor, may be further explored as well as a number of different preoperative indicators linked to psychological status including depression, generalized anxiety or panic disorder measures. This may mean the measure for pain catastrophisation could binarize the results of the pain catastrophisation score into a 'high' or 'low' bin and may result in segmenting the highest tertile of the patient population into the high pain catastrophisation population group. This example may also take the route of characterizing its results in a logistic regression with its improvement scenario based off a percentage gain on the initial state.

It is important to note the continued role surgical factors and surgical incidents, including infection rates, ROM achieved on the table while operating, to some degree achieved alignment (in so far as extreme mal-alignment may cause a negative impact) and surgeon training and volume of operations are all drivers of patient outcome not available at the time of making a preoperative outcome prediction, and so there may be a level of 'gap' that predictive models may not close. Prolonged operating time as a broad catch all predictor for surgery complications also has predictive power, though the causality that results is unknown and might be inappropriate if acted on directly.

There are five dimensions across which separate contexts are prevented from being synthesized into effective clinical tools.

The first of this is the target population, with significant variations observed across fundamentally different healthcare regimes that affect a patient's surgical experience and characterize the demographics for the relevant patient groups selected (that is, it is not just how the patient's experience in receiving a joint replacement but who was able to receive a joint replacement in each country.)

The second is the nature of the PROMS or satisfaction metric used and protocol biases in how it is applied (self-administered vs guided, for example.)

The third is whether satisfaction itself or PROMS are actually the target metric at all, as these correlations have been shown to be moderate to weak and the functional and pain states of the patient postoperatively contribute holistically to satisfaction.

The fourth is how a successful PROMS result is defined and whether it is an absolute outcome score that can be considered to succeed or a relative improvement from a preoperative state.

Finally, the use of different instruments in defining the predictor variables and confusion about the constructs they represent, particularly in the psychological area makes comparison of studies with disparate results even more troublesome.

One facet of the patient's disease state that functional instruments seek to capture is the degree of impairment and lost mobility brought on by OA. Patient activity levels may be undertaken using subjective self assessment using a number of different developed scales or, surgeon 'demand matching' of the patient.

Subjective self reported measures of activity and mobility level may vary greatly from objective measures in non predictable ways, however, with sub population trends and variable subject level bias both skewing results. End stage knee osteoarthritis patients may have reduced steps/day counts over healthy comparable age subjects, dropping from about 8800 steps at peak to 6600. These figures are variable within and between patient population groups, however, with delimitations such as public vs. privately treated patients, age and gender all creating enormous variance. Seemingly at odds with this variation is the observation that only 3 days of active measurement are required to elicit a patients activity level profile when assessing step count, which would seem to dispute the idea that patients will change behaviour on weekends vs weekdays and other distinguishing factors.

The objective measurement of activity level can be done in a number of ways. Step count is the most directly applicable to patient lifestyles, to the point where in rheumatoid arthritis sufferers it can be used as an assessment of treatment outcome. Other examples look at activity monitor data as defined by some other metric than step count, including the % of the day the subject spent moving or upright.

Such measures can be considered to be measuring different constructs to step count, however, as it is not difficult to imagine a scenario in which subjects who are active and walking for the same amount of time achieve different step counts based on gait speed. Other examples use accelerometry based at specific points, and correlate accelerometry data from the tibial tubercle to patient reported knee instability. Gait analysis may also be useful. Step count has a significant advantage in that the variable it introduces is readily understood and so empowers patient self management of their disease state.

Wearable wireless activity monitors such as the Fitbit are an increasingly low cost, clinically relevant off the shelf option for monitoring patient activity levels. These devices may be valid and reliable assessment tools for ambulation in normal subjects specifically, and the whole field of pedometry generally may have similar effectiveness. Other examples exploit the value of wireless activity monitors in chronic disease assessment The period over which the devices where worn may be 48 hours.

One example reports on energy expenditure quantification based on an intelligent activity monitoring device. This may comprise a measure of activity level over 5 different recording periods, covering preoperative, 6 week, 3 month, 6 month and 12 month scenarios. This may allow for a single value that is patient relevant, understandable and readily intervenable by patients in a self managed way to be reported, an argument that has been noted previously.

The device may measure the amount of time spent walking as a percentage of daily activity and there may be an implicit relationship between time spent walking, speed of gait and amount of steps being undertaken. As a demonstrative example, a patient who had spent 5% of the day walking pre and postoperatively, whose gait speed was twice as fast postoperatively, would count twice as many steps with a pedometer in the postoperative scenario but the same amount of time spent walking. Other examples assess patients over a 4 to 7 day period using a relatively small and unobstructive waist mounted device and so represent an attempt to overcome some of the potential observation bias. This may comprise sampling differences, including a BMI.

These measures could be used as an assessment target for early recovery interventions designed to drive patient self-efficacy, and so with such a structure a clinical improvement mechanism could be generated.

One example are BBN models. Particularly appealing in this structure is the relative ease with which expert knowledge modeled observations can be pulled into the model to enhance its predictive capacity and avoid some of the issues associated with the fractured nature of the available data in the literature. These observations can be pulled from either expert individuals, teams or through literature meta analysis.

As a further point, Bayesian models have an additional advantage in that the Bayesian Network structure can be quite insensitive to variation of precision of diagnosis.

Health care systems have a finite pool of resources in which to provide care to its citizens. Total knee arthroplasty is a surgery that is associated with high costs and a high rate of dissatisfaction at one year post operatively. Health care systems may benefit from a means in which the cost of a knee replacement is a) predictable for each patient and b) presents a pre and post-operative plan that is both cost effective and benefit maximising for patients. Stratification of patient care based on predictions of outcome pre and post operatively may offer a solution in which resources are effectively utilised pre and post total knee arthroplasty.

Stratification of care structures may benefit from a suite of targeted intervention strategies with known or predictable impacts on patient outcome. Using preoperative and postoperative data collection from patients may be one mechanism by which cost effective, patient specific intervention strategies may be targeted at appropriate patients for maximal impact. Linking these observations to a healthcare utility filter may allow for significant savings to be realised, or significant outcome gains to be generated. Some possible approaches to achieving such a health care utility filter may be minimising the cost to the health system with a targeted overall patient satisfaction level, reducing associated individual patient costs with a targeted minimal acceptable predicted outcome per patient or a fixed cost, best allocation system whereby a fixed amount of resources are applied in order to get the highest possible proportion of satisfied patients.

As such, the solution proposed herein may overcome the fractured data landscape by pulling in observations from as many literature sources as possible to enhance an initial, single database fed model, using a team of surgeons to guide the development of the model in order to create as strong a predictor of TKR outcome as possible. Cheaply objectively measurable data sources may be used to substitute subjective data in the field of preoperative functional assessment relying on low cost pedometers in a clinically integrated workflow. The impact of the predictive tool may be assessed by way of expectation measurement of the patient prior to and following a routine surgical consultation in which this may be used to drive an intervention. Further to this, the impact across a patient group may be assessable through cost savings or outcome improvements across the participating patient population, by incorporating further elements described below.

In one example, there is a platform for collection of data from patients in a preoperative setting in order to predict postoperative outcomes in TKR patients against an analytical algorithm. The platform comprises an interface developed for maximal ease of patient use, using a one-question-per-page structure and automatic validation of incoming data where appropriate capable of rendering questions which are Visual Analog Scale
Binary or multiple choice
Open text or number fields
Customizable on a per surgeon, per practice or per site basis
An application to display the interface to the patient, capture patient data and return it securely to a server
Customisation of the outcome to be predicted from patient reported outcomes in functional, activity, quality of life or pain based subdomains, generic/holistic measures of health or specific functional attainments including but not limited to postoperative range of motion, postoperative time to mobilisation and ambulation or activity level and risk of adverse events.

Figure 18:
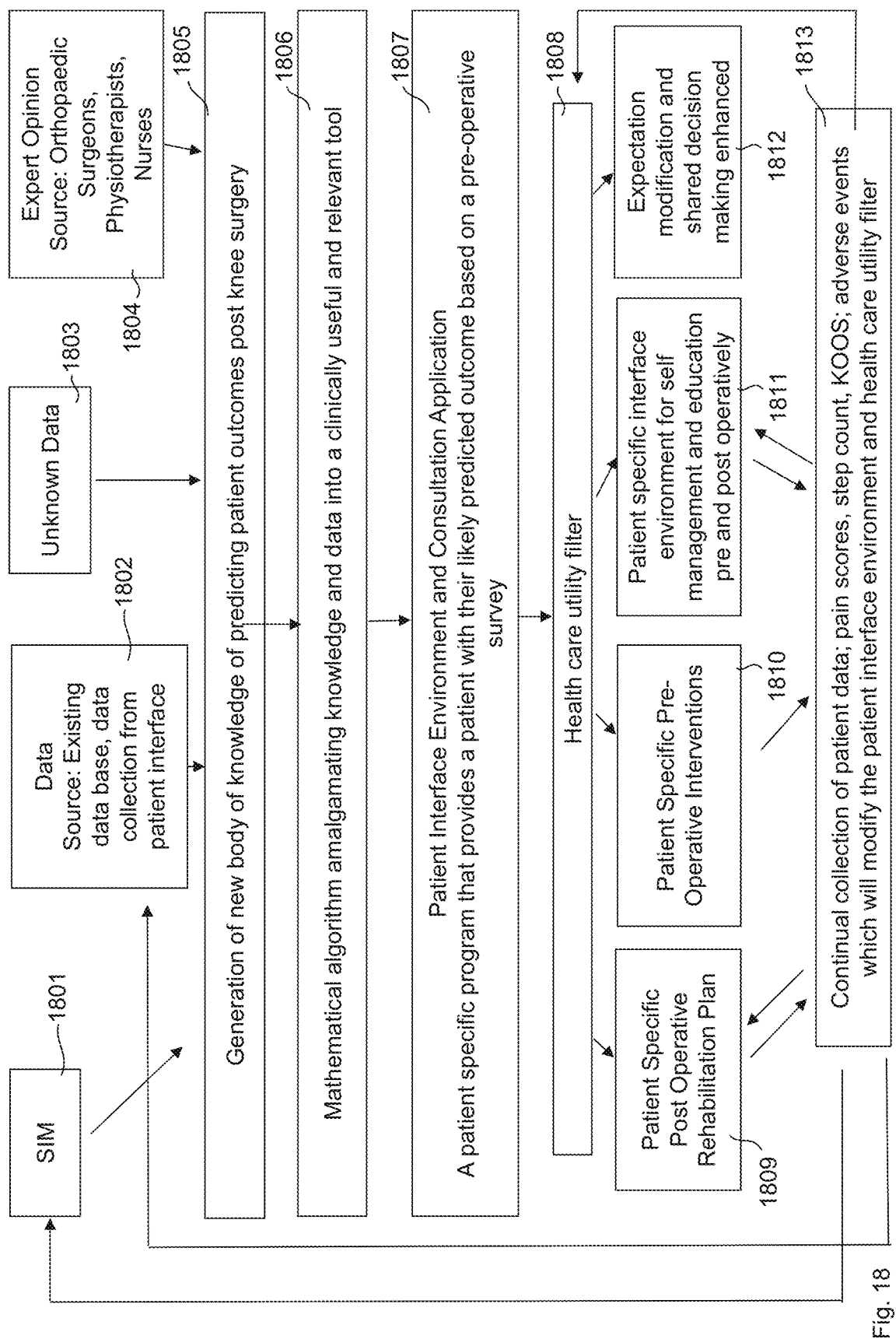
FIG. 18 illustrates an architecture 1800 for managing patients of knee surgeries.

FIG. 18 illustrates an architecture 1800 for managing patients of knee surgeries. Input data of architecture 1800 comprises a simulator data 1801 from a simulator, such as a physical simulator that simulates movement of the bones around the knee joint. Input data further comprises patient data 1802, such as data from existing data bases and data collected from patient interfaces described herein. Input data further comprises unknown data 1803 and expert opinion data 1804 from orthopaedic surgeons, physiotherapists and nurses, for example.

A knowledge generation module 1805 receives the input data 1801, 1802, 1803 and 1804 and generates a new body of knowledge of predicting patient outcomes post knee surgery. An amalgamation module 1806 amalgamates, based on a mathematical algorithm, the knowledge and data into a clinically useful and relevant tool. In particular, the amalgamation module 1806 determines the conditional dependencies between the input data, such as the patient input data, and the predicted satisfaction value as stored associated with the edges of the statistical model.

A patient interface module 1807, such as a patient interface environment and consultation application, generates a user interface comprising a patient questionnaire and evaluates the statistical model to determine a predicted patient satisfaction value as described herein with reference to FIG. 2, for example. That is, a patient specific program provides a patient with their likely predicted outcome based on a pre-operative survey.

The output data of the patient interface module 1807 is provided to a filter module 1808, such as a health care utility filter, which determines an action based on the predicted satisfaction value.

The filter module 1808 may activate a rehabilitation plan module 1809 that determines a patient specific post-operative rehabilitation plan. For example, the rehabilitation plan module 1809 may query a look-up table to find a pre-configured rehabilitation plan for a particular predicted satisfaction value.

The filter module 1808 may further activate a interventions module 1810 that determines patient specific preoperative interventions. Again, processor may query a lookup table to find appropriate interventions.

The filter module 1808 may further activate patient guidance module 1811 that generates a patient user interface environment for self-management and education pre- and post-operatively. For example, the patient user interface may display instructions containing text, images and videos for knee-related and patient specific exercises and provide input fields that allow the patient to indicate the completion of those exercises.

Filter module 1808 may further activate a modification module 1812 that modifies expectations and enhances shared decision making, such as by informing the patient or the surgeon or allow the surgeon to collaborate with other surgeons to improve the expected outcome of the knee surgery.

Architecture 1800 further comprises a data collection module 1813 that continually collects patient data, such as pain scores, step count, KOOS. Data collection module 1813 may further collect data indicative of adverse events which will modify the patient interface environment 1811 and health care utility filter 1808.

Architecture 1800 is described as comprising several modules and each module may be a piece of software, such as a C++ or Java class or may be its own application executed by its own processor on its own device. The arrows in FIG. 12 may be implemented by way of function parameters, class parameters, inter-process communication, TCP/IP communication over the internet or another distributed computing platform, such as a cloud computing platform.

FIG. 19 illustrates a model selection user interface 1900 as generated by processor 102. The model selection user interface 1900 comprises multiple indications associated with respective models. For each model, the user interface 1900 shows the name of the surgeon, the name of the hospital, the number of patients used to train the model and the cost.

Each of the models is associated with different conditional dependencies between the nodes of the statistical model as learned from the data from the number of patients.

Processor 102 receives from a surgeon user input in relation to one or more of the multiple indications associated with one or more of the models, such as an indication of the surgeon pressing one of the 'select' buttons.

Processor 102 determines a price value associated with the one or more of the models, such as by retrieving the price value from a data base of models. Processor 102 then generates a payment interface for the determined price value, such as by calling a payment processor API, such as the PayPal API or Google Wallet API.

Once processor 102 receives a payment confirmation from the API, processor 102 enables the evaluation of the selected model, that is, processor 102 allows the patient data to be fed into the nodes and edges to determine the predicted satisfaction value.

Simulation System

The following disclosure provides a description of a kinematic simulation system that uses multiple loaded X-ray images. It is noted, however, that the methods described herein for applying a machine learning model to mechanical parameters equally applies to a kinematic simulation based on a single CT scan disregarding the individual's characteristics of ligaments.

The joint comprises a kinematic system of two bones, such as the tibia and femur in the example of knee surgery or hip and femur in the example of hip surgery. The kinematic system may comprise more than two bones including the patella, for example.

Figure 20:
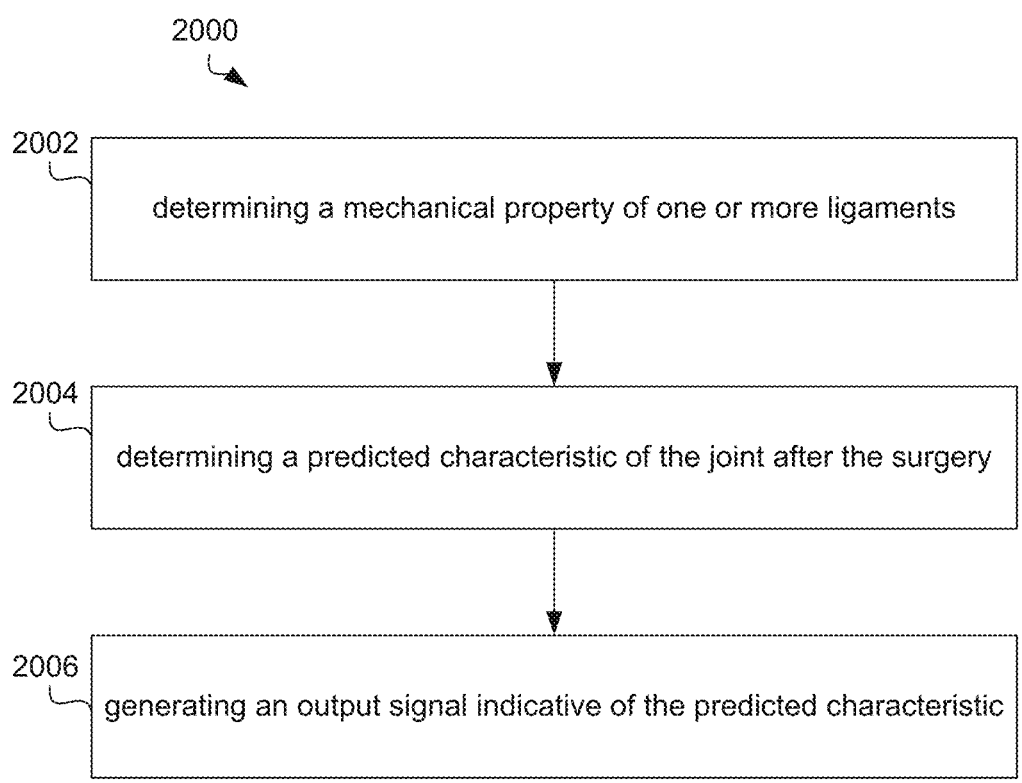
FIG. 20 illustrates a method for kinematic simulation.

FIG. 20 illustrates a method for kinematic simulation. Processor 102 commences performing method 2000 by determining a mechanical property of one or more ligaments associated with the joint. For example, processor determines a stiffness and a length value, which may be a free length, a reference length or a taut length. This calculation is based on measurement data indicative of a movement of the bones relative to each other under multiple mechanical loads. In one example, processor 102 determines the measurement data based on multiple X-ray images, which are also referred to as 'first' images, and an MRI image, that is also referred to as 'second' image.

It is to be understood that 'image' may refer to a two-dimensional image, such in X-ray image stored on data memory 106 in the form of a two-dimensional pixel matrix comprising one intensity value for each pixel in the case of a grey scale image. However, 'image' may also refer to a three-dimensional image comprising multiple two-dimensional images, such as an MRI or CT image which a surgeon can peruse on a two-dimensional screen by selecting different depth values and different viewing angles. Two-dimensional and three-dimensional images may be stored on data memory 106 as multiple image values, such as in a two-dimensional or three-dimensional pixel matrix. In other examples, the images are stored in a parameterised representation, such as a spline representation and processor 102 generates a two-dimensional view on a screen by interpolation based on the spline parameters.

Figure 21A:
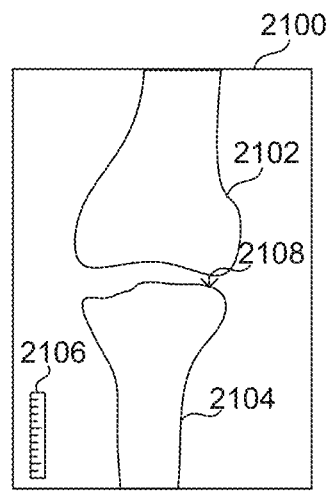
FIG. 21a illustrates an X-ray image of a knee joint in an unloaded state.

FIG. 21a illustrates an X-ray image 2100 of a knee joint in an unloaded state, that is, the patient is lying without externally applied forces. X-ray image 2100 shows the femur 2102 the tibia 2104 and an absolute reference 2106 that was place next to the knee when taking the X-ray image. Processor 102 detects the edges of the femur 2102 and tibia 2104 using a Sobel operator, for example. In another example, processor 102 performs a method for 2D-3D image registration as described in the following publications, which are incorporated herein by reference:

Youngjun Kim, Kang-Il Kim, Jin hyeok Choi, Kunwoo Lee, "Novel methods for 3D postoperative analysis of total knee arthroplasty using 2D-3D image registration", Clinical Biomechanics 26 (2011) 2184-2191;

Guoyan Zheng, Xuan Zhang "Computer assisted determination of acetabular cup orientation using 2D-3D image registration", International Journal of Computer Assisted Radiology and Surgery, September 2010, Volume 5, Issue 5, pp 437-447; and Guoyan Zheng, Simon Steppacher, Xuan Zhang, Moritz Tannast, "Precise Estimation of Postoperative Cup Alignment from Single Standard X-Ray Radiograph with Gonadal Shielding", Medical Image Computing and Computer-Assisted Intervention—MICCAI 2007, Lecture Notes in Computer Science Volume 4792, 2007, pp 951-959.

Processor 102 then determines a minimum distance 2108 between the femur 2102 and tibia 2104 as a number of image pixels. Processor 102 can then detect the absolute scale 2106 to transform the number of image pixels into an absolute measurement in millimetres, for example.

Figure 21B:
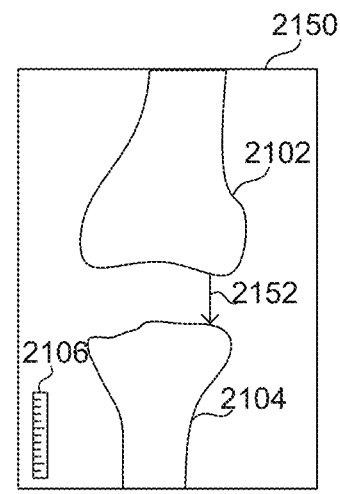
FIG. 21b illustrates an X-ray image of the knee joint in a loaded state.

FIG. 21b illustrates an X-ray image 2150 of the knee joint in a loaded state. In this example, the patient is standing on one leg on a step and a weight is attached to the foot of the other leg that is relaxed and hangs off the step. As can be seen in FIG. 3b there has been movement of the femur 2102 and the tibia 2104 relative to each other under the two different mechanical loads, that is, a movement between FIG. 3a and FIG. 3b. Again processor 102 detects the edges of femur 2102 and tibia 2104 and determines a minimum distance 2152 in millimetres between them. Processor 102 can then calculate the change in distance from 2108 to 2152 as well as rotation difference, which is indicative of the relative movement of the femur 2102 in relation to the tibia 2104 or vice versa.

Since the distance 2152 under load depends on the mechanical characteristics of the ligaments, processor 102 can determine these mechanical characteristics based on a mechanical model and the measured distances 2108 and 2152.

Figure 22A:
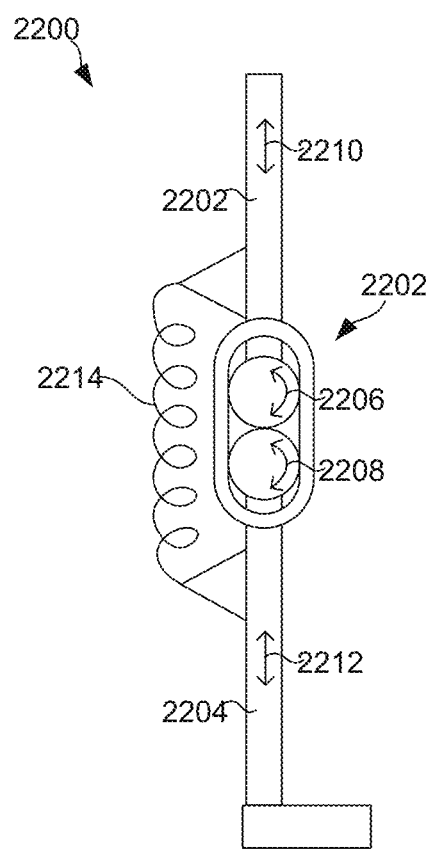
FIG. 22a illustrates a simplified mechanical model of the knee in the unloaded state.

FIG. 22a illustrates a simplified mechanical model 2200 of the knee in the unloaded state related to X-ray image 2100 while FIG. 4b illustrates the mechanical model of the knee in a loaded state related to X-ray image 2150. In this example, the mechanical model 2200 comprises an upper rod 2202 representing the femur 2102 and a lower rod 2204 representing the tibia 2104. The two rods 2202 and 2204 are mechanically coupled by a joint 2202 that allows rotation with one degree of rotational freedom as indicated by arrows 2206 and 2208 to model the flexion and extension of a human knee. Joint 2202 also allows translational movement with one degree of freedom as indicated by arrows 2210 and 2212 to represent stretching of the knee under load. The translational movement 2210 and 2212 is restricted by a spring 2214, that is, spring 2214 pulls the upper rod 2202 towards the lower rod 2204 with a force that increases with the distance between the upper rod 2202 and the lower rod 2204.

Figure 22B:
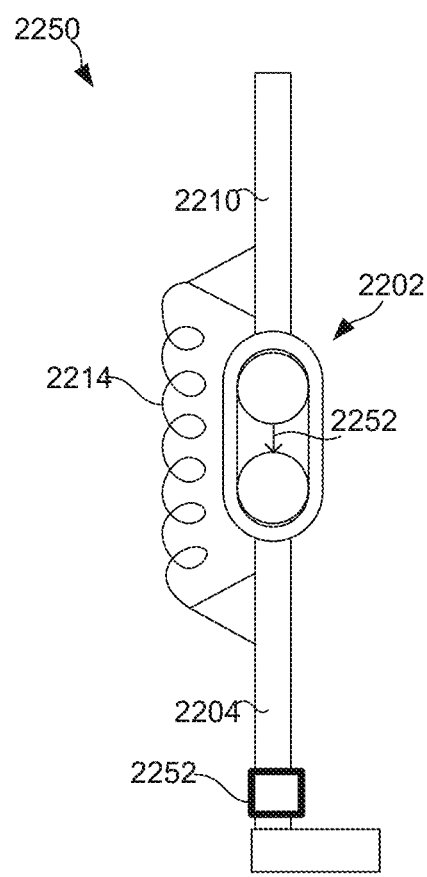
FIG. 22b illustrates the mechanical model of the knee as in FIG. 22a but now the mechanical model is under load.

FIG. 22b illustrates the mechanical model 2200 of the knee as in FIG. 22a but now the mechanical model is under load as shown in X-ray image of FIG. 3b. FIG. 22b illustrates a weight 2252 that is attached to the lower rod 2204. As a result of the weight 2252 there is translational movement of the lower rod 2204 in relation to the upper rod 2202 against the pull force of spring 2214 resulting in a distance 2252 in the joint 2202. In this example, it is assumed that the distance in the joint is zero in the unloaded case in FIG. 22a for simplicity.

The force F applied by spring 2214 with spring constant k at length x is F=−kx, which can be re-arranged to $$k = \frac{-F}{x}.$$

F is the force applied by weight 2252, such as 5 kg, and x is the measured movement 2252, both of which are stored on data memory 106. As a result, processor 102 can determine the spring constant k, which is also referred to as the stiffness value of the ligament. By setting the value for F to zero, processor 102 can also calculate the free length, which is the result for x given the determined spring constant k and F=0.

While the example of FIGS. 22a and 22b relates to determining the stiffness of only a single ligament, in other examples processor 102 determines the stiffness of multiple ligaments. For example, the knee can be separated into three physiological anatomical compartments: the patellofemoral compartment, the medial compartment, and the lateral compartment. The lateral compartment is bounded medially by the anterior cruciate ligament, laterally by the lateral capsular ligament, the ilio-tibial tract, and the fibula lateral ligament and posteriorly by the arcuate complex and the posterior capsule. These structures are all supported by the iliotibial band, the poplitius muscle, the biceps muscle and an extension of the semimembranosus muscle called the oblique popliteal ligament.

The medial compartment is bounded medially by the deep third of the mid-capsular ligament, the medial collateral ligament, and the posterior oblique ligament and laterally by the posterior cruciate ligament. Anteriorly, these compartments have extensions of the medial capsule as well as patellotibial and patellofemoral expansions, as well as the patella tendon.

Since each ligament may have a different stiffness value and free-length value, processor 102 may determine the movement 2152 for multiple different mechanical loads. Each ligament generates another unknown in a linear system of equations based on the above formula and each measurement of a different load generates an observation. Preferably, the number of different loads is at least the number of ligaments. Further, the accuracy can be increased by having each linear equation linearly independent from the other equations. Therefore, the load may be applied to the knee at different flexion angles of the knee such that different ligaments are stretched at different angles.

The measurement data may comprise data generated by a stress device that applies the different mechanical loads to the knee. In one example, the stress device is a Telos stress device by Austin & Associates, Inc./Telos GmbH. It is noted that other devices may also be used to generate the measurement data.

Before processing the X-ray images of the loaded knee, processor 102 may determine the attachment locations of each ligament to the bone and the shape and size of the bones to refine the mechanical model 2200. For example, the processor 102 may process an MRI scan of the bone. The ligaments are clearly visible on MRI but hardly visible on an X-ray image. However, it is difficult to apply mechanical force to the knee while taking an MRI scan due to the relatively long time the MRI scan takes and due to the strong magnetic field of the MRI scanner. Therefore, the MRI is only captured once to define the static characteristic of the joint, including the 3D geometries and landmarks from which to measure the movement, such as medial and lateral condyles. Then, multiple X-rays are captured at different loads and flexion angles.

Instead of the single distance measurement 2152 of FIG. 21b, the measurement data may include multiple measurements for each mechanical load, such as distances from medial and lateral condyles to the tibia to define vargus and valgus. Processor 102 may further calculate a pre-operative characteristic of the knee, such as pre-op laxity.

Returning back to FIG. 20, after the mechanical properties of the ligaments are determined, processor determines 2004 a predicted characteristic of the joint after the surgery, such as predicted post-op laxity. This step is based on a spatial parameter of the surgery and based on the previously determined mechanical property of the one or more ligaments. The surgery may comprise the insertion of an implant, which likely affects the three-dimensional geometries of the joint. In particular, the cut angle of the tibia on which the implant is mounted is an important spatial parameter that affects the angles of the knee. Other spatial parameters relate to the geometry of the particular implant. This geometry may be retrieved from an implant library that stores the geometries of a wide range of available implants. Processor 102 receives the data indicative of the planned cut angle and the geometries of the implant. Based on this data and the mechanical characteristic of the ligaments, processor 102 calculates a predicted characteristic of the knee after the surgery. That is, processor 102 applies the same loads as above on the mechanical model considering the determined ligament properties but now for a changed geometry as a result of the planned surgery. For example, processor 102 determines the post-operative varus/valgus values and post-operative laxity of the knee joint using spring constants k and new geometries.

Processor 102 then generates 2006 an output signal indicative of the predicted characteristic to assist the surgery. In one example, the output signal is a display to be shown to the surgeon on a computer screen. The display may comprise numbers representing the determined varus/valgus at different stress test or may comprises a graphical indication of predicted post-operative laxity, such as curves of varus/valgus at applied moments to the model at different flexion angles. This informs the surgeon on whether the planned parameters of the operation are satisfactory or whether the cut angle for the implant should be adjusted, for example.

For example, the surgeon may perform a surgical technique called gap balancing where the surgeon cuts the tibia surface first then distracts the joint to find balance. Then the femoral component alignment, particularly rotation, is planned accordingly to achieve that balance. However, the definition of balance may differ between surgeons and may be subjective. By measuring the applied force or pressure during the joint distraction, processor 102 can generate an output signal that objectively indicates to the surgeon how to balance the knee based on the mechanical simulation model.

In another example, the output signal to assist the surgery is a feedback signal to a planning software that automatically optimises the spatial parameters, such as iteratively adjusts the cut angle until the output signal is indicative of a desired laxity. In that example, the surgeon may enter an intended cut angle which is received by the processor 102 as a predefined value of the spatial parameter of the surgery. If the output signal generated by processor 120 is indicative of an unsatisfactory laxity, the planning software adjusts the pre-define value to optimise the laxity.

In yet another example, the surgeon enters a desired laxity or the planning software determines a desired laxity based on particular activities that the patient wants to perform after the surgery. For example, kneeling down would be easier with a less tight knee, that is, more laxity, while playing tennis would be easier with a tighter knee, that is, less laxity. The output signal is then indicative of whether the predicted characteristic corresponds to the desired characteristic, such as by highlighting in red colour the values for relative movement or angles when processor 102 applies forces to the mechanical model as described above. The output signal may also be a data signal representing a report of the predicted characteristic of the joint after surgery. The report may also include the pre-operative characteristic.

Figure 24:
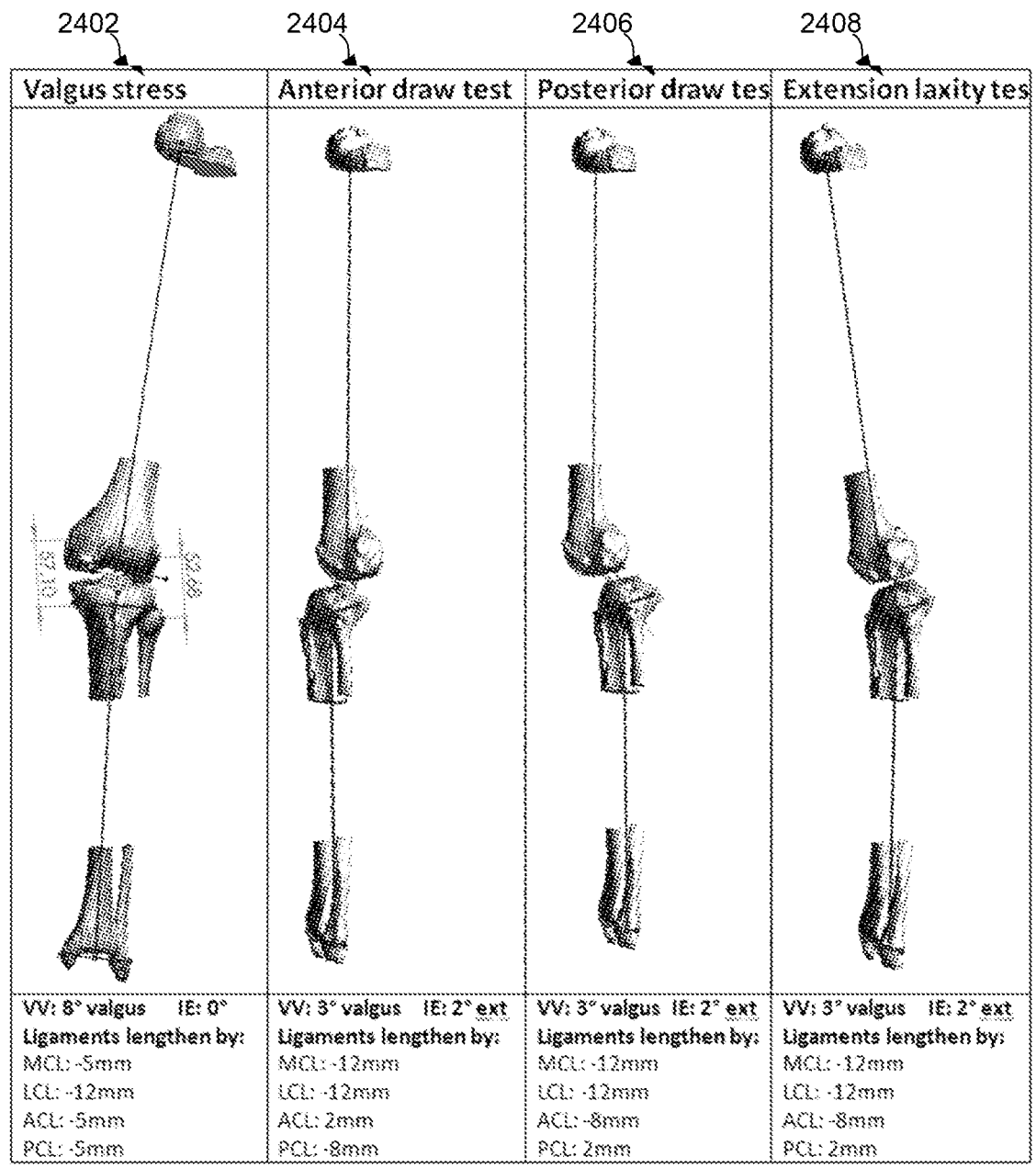
FIG. 24 illustrates the mechanical model of the knee under four further different mechanical loads.

FIG. 23 illustrates a mechanical model of a knee under three different mechanical loads, that is, while one leg is hanging 2302, when the knee is weight bearing 2304 and under varus stress 2306. FIG. 24 illustrates the mechanical model of the knee under four further different mechanical loads, that is, valgus stress 2402, anterior draw test 2404, posterior draw test 2406 and extension laxity test 2408.

Figure 25A:
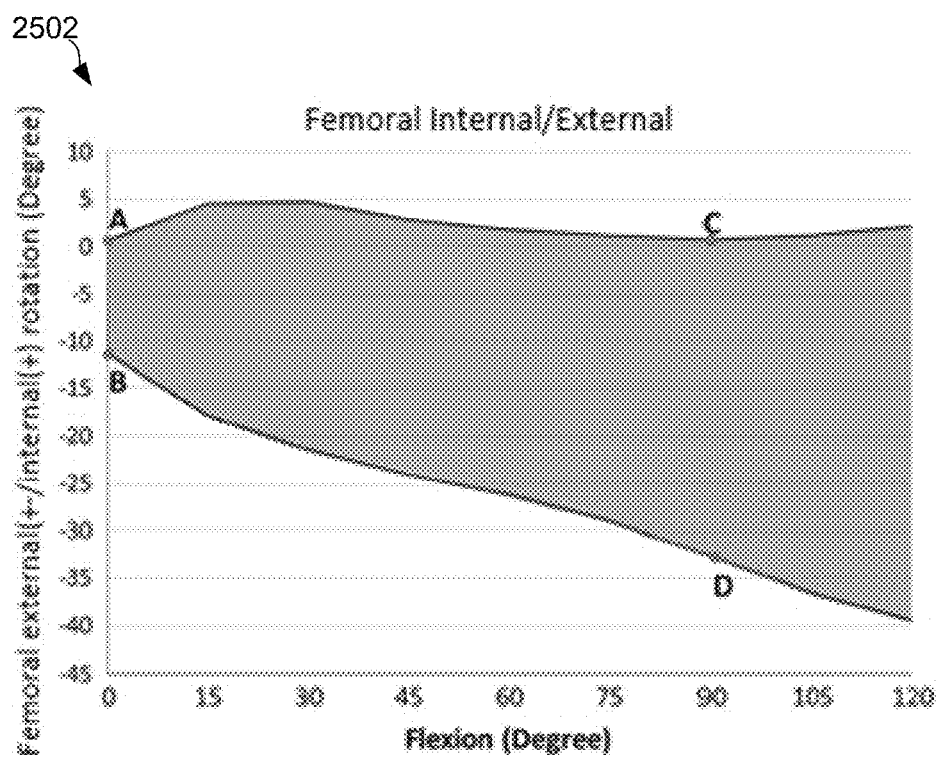
FIGS. 25a, 25b and 25c illustrate laxity envelopes for femoral internal/external rotation, femoral varus/valgus and anterior/posterior laxity, respectively.
Figure 25B:
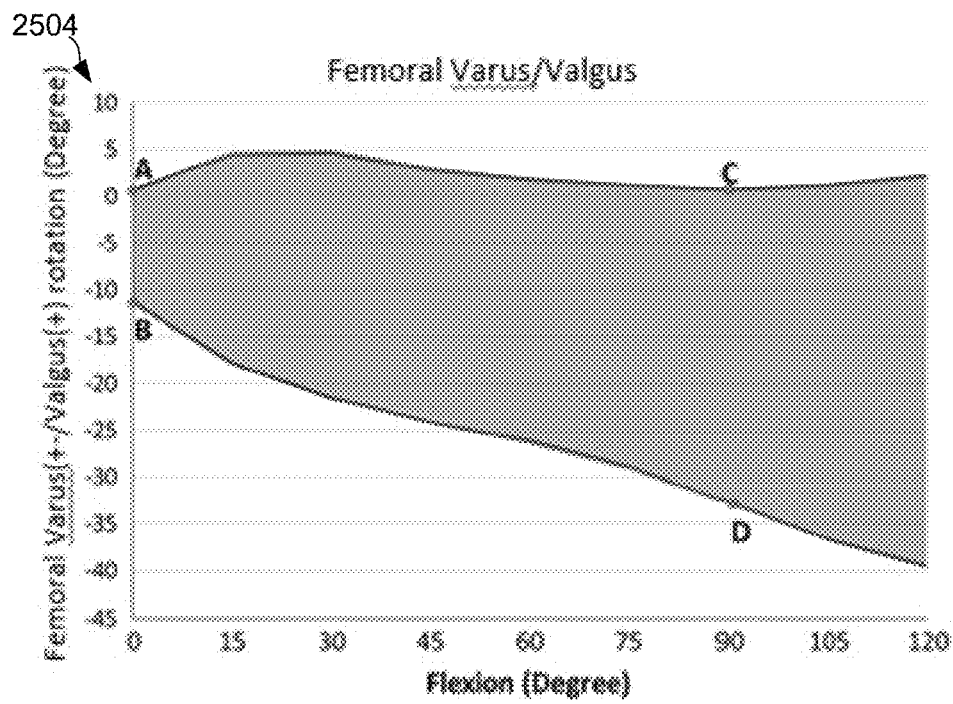
Figure 25C:
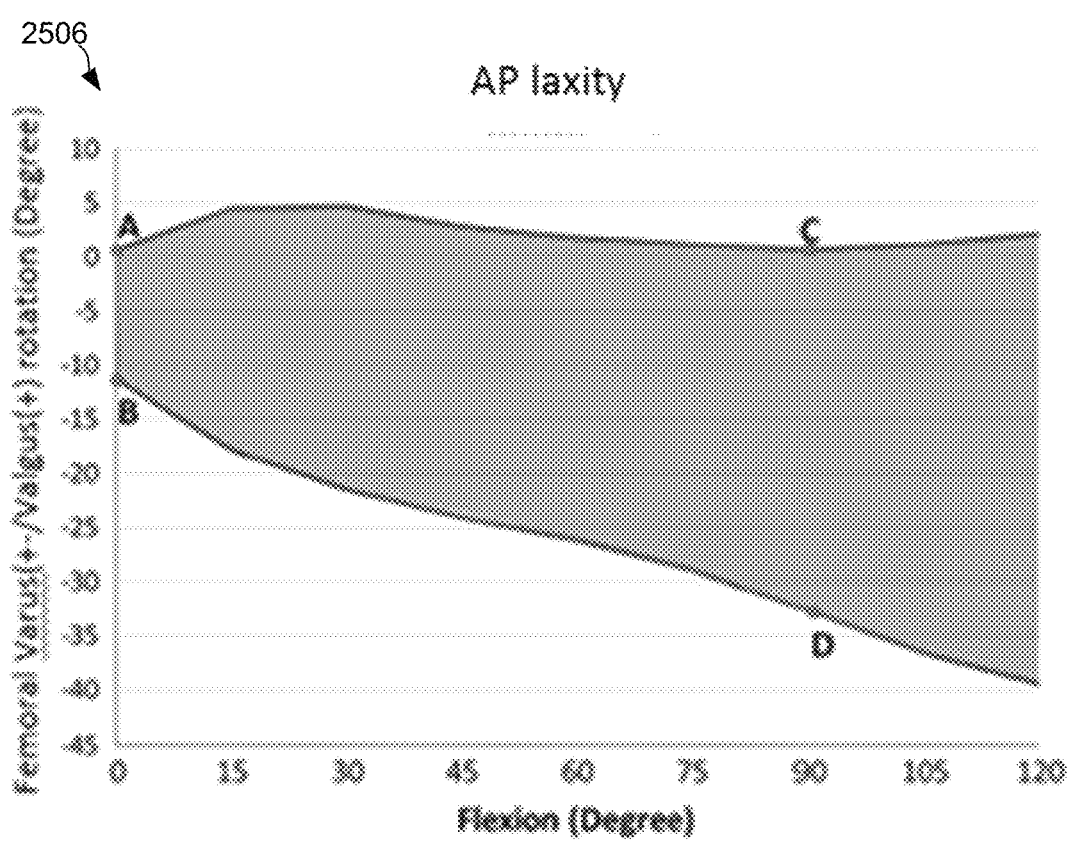

FIGS. 25a, 25b and 25c illustrate laxity envelopes for femoral internal/external rotation 2502, femoral varus/valgus 2504 and anterior/posterior laxity 2506, respectively, over a range of flexion from 0 to 120 degrees.

In one example, the ligament laxity order is:

| Ligaments | Tight by percentage |
|---|---|
| LCL | 20% |
| MCL | 10% |
| PCL | — |

Implant System Details may be
Femoral Component: Omni Apex Right CR Femur Size 5
Tibial Component: Omni Apex Tibial Tray Size 6
Tibial Insert: Omni Apex CR Insert Size 5 10 mm
Patella Button: Omni Apex Patella Button Size 35 8 mm
Component Placement Information may be:

| | Femoral Component | Tibial Component | TibioFemoral Alignment |
|---|---|---|---|
| Sagittal: | 4.0° Flexion | 3.0° Slope | |
| Coronal: | 0.0° Varus | 0.0° Varus | 0.0° Varus |
| Transverse: | 0.0° Internal | 0.0° Internal | 0.0° Internal |
| AP position | 2 mm anterior from PCA | Best fit to resected tibia geometry | |
| SI position | Level with distal condyle | 11 mm cut from medial plateau | |
| ML position | Best fit to resected geometry | Best fit to resected geometry | |

FIGS. 26a to 26f graphically illustrate the predicted characteristic of the knee after surgery in the form of rendered images of the mechanical model of the knee for the load of 6 Nm applied to the model. FIGS. 26a to 26c relate to full extension, while FIGS. 26d to 26f relate to a fully flexed knee. For example, the surgeon can clearly see that a varus torque of 6 Nm results in a predicted varus of 3 degrees at full extension (see FIG. 26a and a varus of 4 degrees at full flexion (see FIG. 26d). Further, the unloaded knee is balanced at full extension, that is has 0 degrees varus/valgus (see FIG. 26b) but has a 1 degree varus at full flexion (see FIG. 26e).

Figure 27:
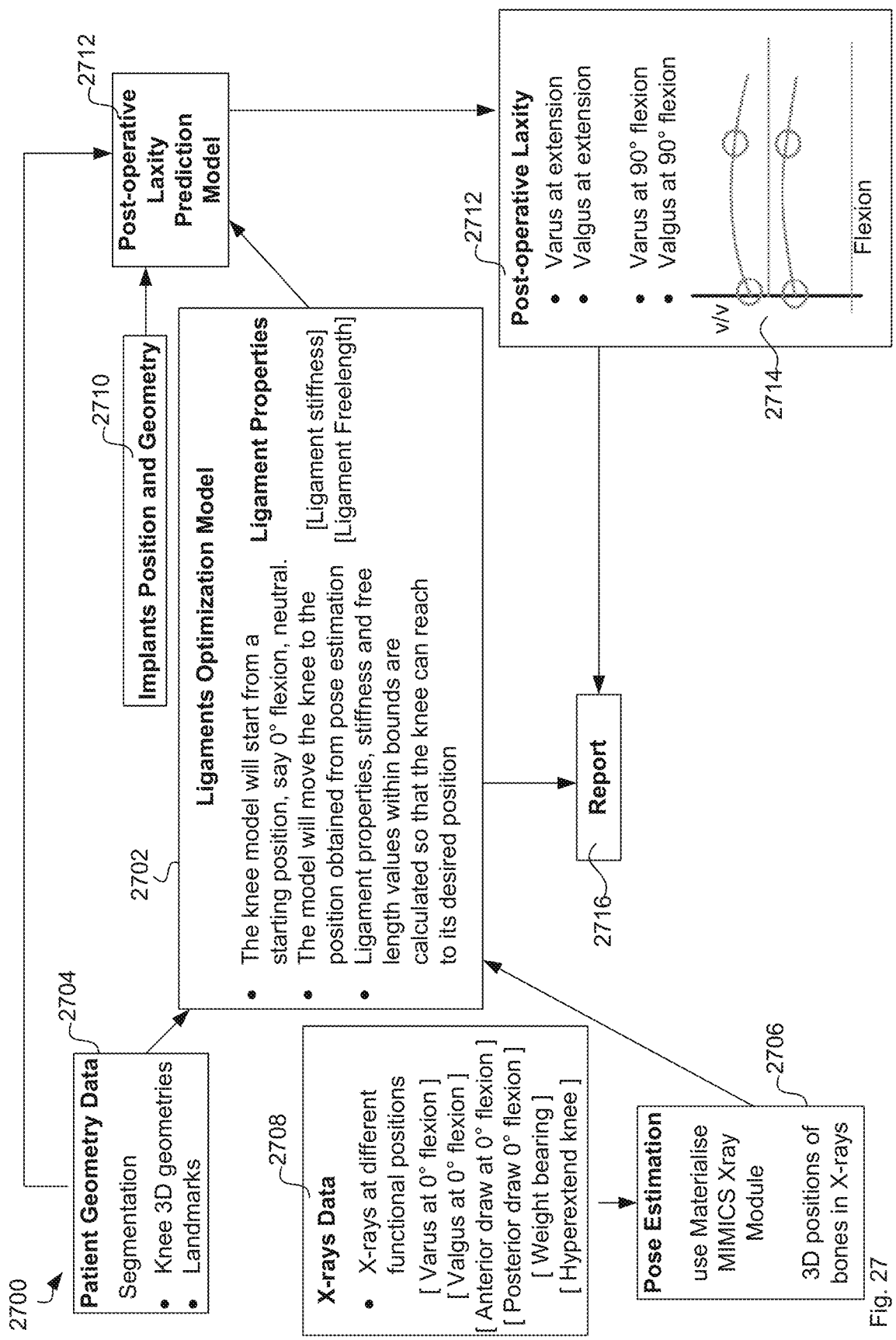
FIG. 27 illustrates a more detailed version of method in FIG. 20 in the form of a flow chart.

FIG. 27 illustrates a more detailed version of method 2000 in the form of a flow chart 2700. The flow chart 2700 may also be implemented by corresponding software modules. The central module is a ligaments optimisation module 2702 that optimises the mechanical properties of the ligaments to best fit to the observations of the movement of the bones under different mechanical loads. For these calculations ligaments optimisation module 2702 receives patient geometry data from a patient geometry data module 2704. The ligaments optimisation module 2702 further receives measurement data, such as the three-dimensional position of bones in X-rays under different load conditions from pose estimation module 2706. The pose estimation module 2706, in turn, receives the X-ray data from X-ray data module 2708, such as X-ray images at different functional positions including one or more of: Varus at 0° flexion, Valgus at 0° flexion, Anterior draw at 0° flexion, Posterior draw 0° flexion, Weight bearing and Hyperextend knee.

Figure 28A:
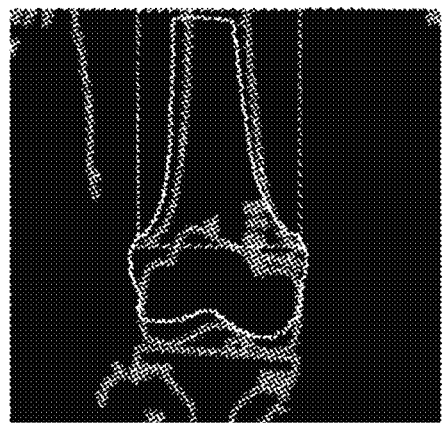
FIGS. 28a to 28d illustrate the registration step between the X-ray image data and the mechanical model.
Figure 28B:
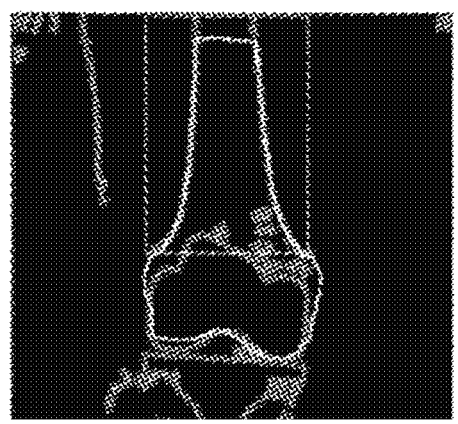
Figure 28C:
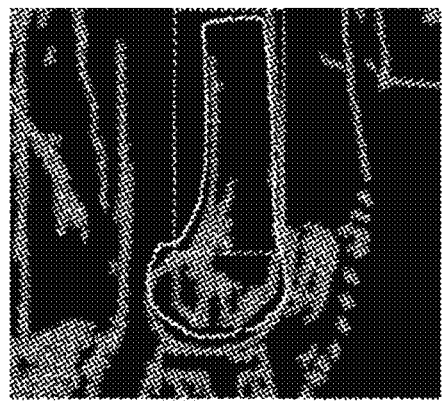
Figure 28D:
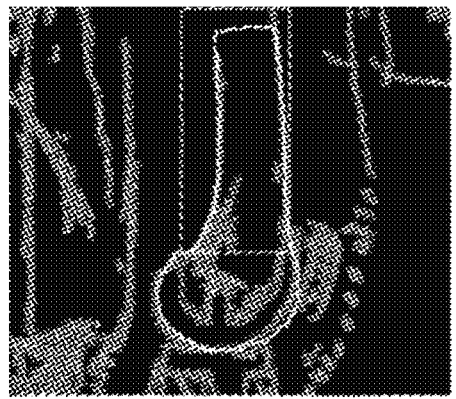

FIGS. 28a to 28d illustrate the registration step between the X-ray image data as schematically shown in FIGS. 21a and 21b and the mechanical model in FIGS. 22a and 22b. In this example, the image data is registered to a femur model. The X-ray image data in darker shading, while model outline is shown in brighter shading. This registration step may be part of the steps for determining the measurement data indicative of a movement of the bones relative to each other under multiple mechanical loads. FIGS. 28a and 28c illustrate the image data and the model before registration while FIGS. 28b and 28d illustrate the image data and the model after registration where the femur model matches the X-ray image data.

Figure 29:
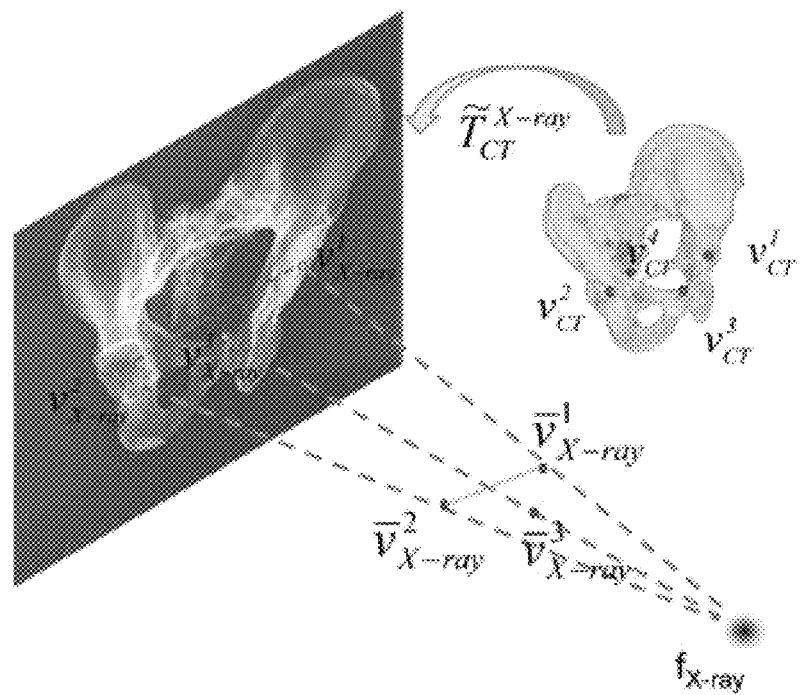
FIG. 29 illustrates an initialisation of an iterative landmark-to-ray 2D-3D registration.
Figure 30:
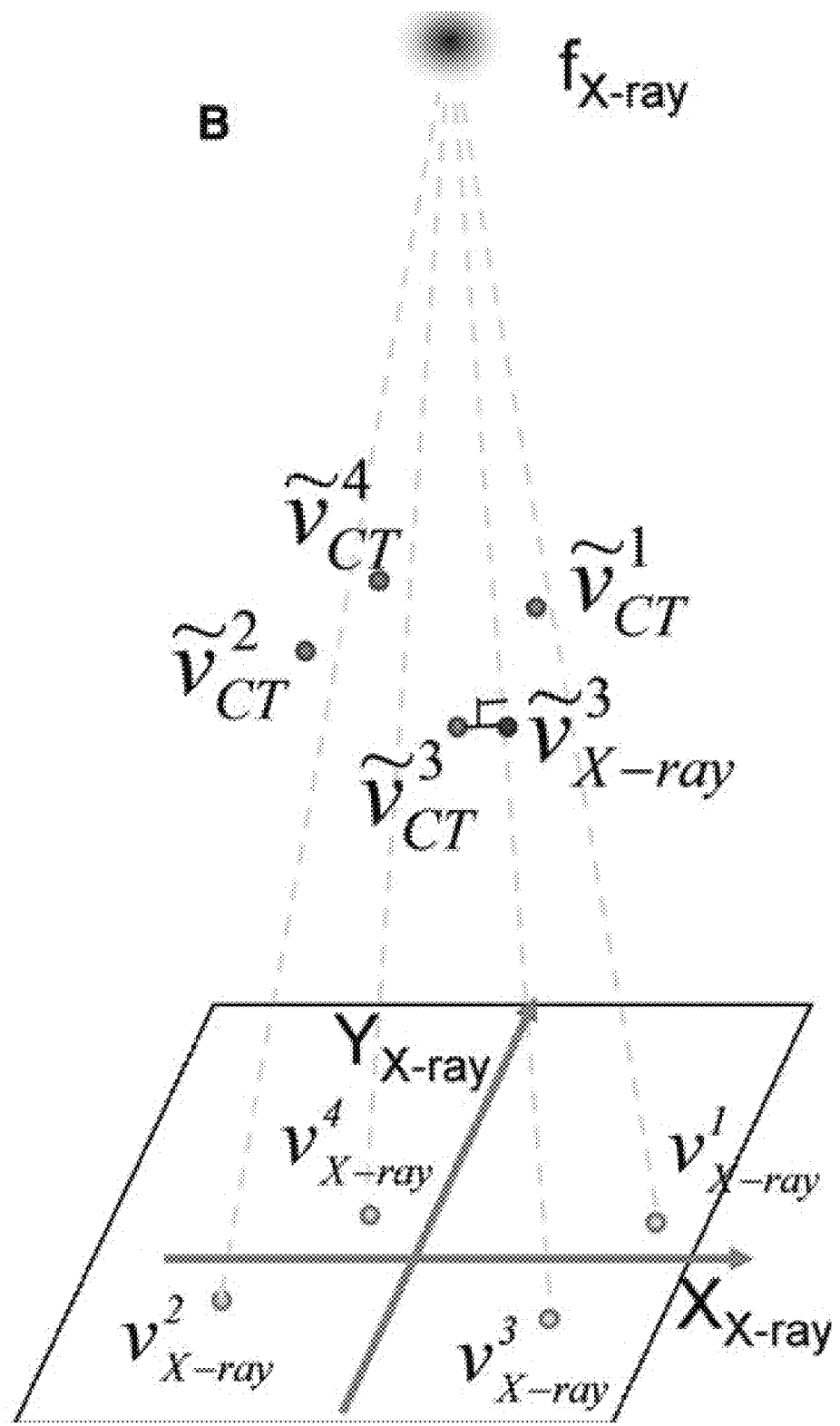
FIG. 30 illustrates finding 3D point pairs for the iterative landmark-to-ray 2D-3D registration.

FIG. 29 illustrates an initialisation of an iterative landmark-to-ray 2D-3D registration, while FIG. 30 illustrates finding 3D point pairs for the iterative landmark-to-ray 2D-3D registration.

The knee optimisation module 2702 may start from a starting position, such as 0° flexion, neutral moves the knee to the position obtained from pose estimation. Processor 102 calculates ligament properties, stiffness and free length values within bounds so that the knee can reach to its desired position.

Figure 31:
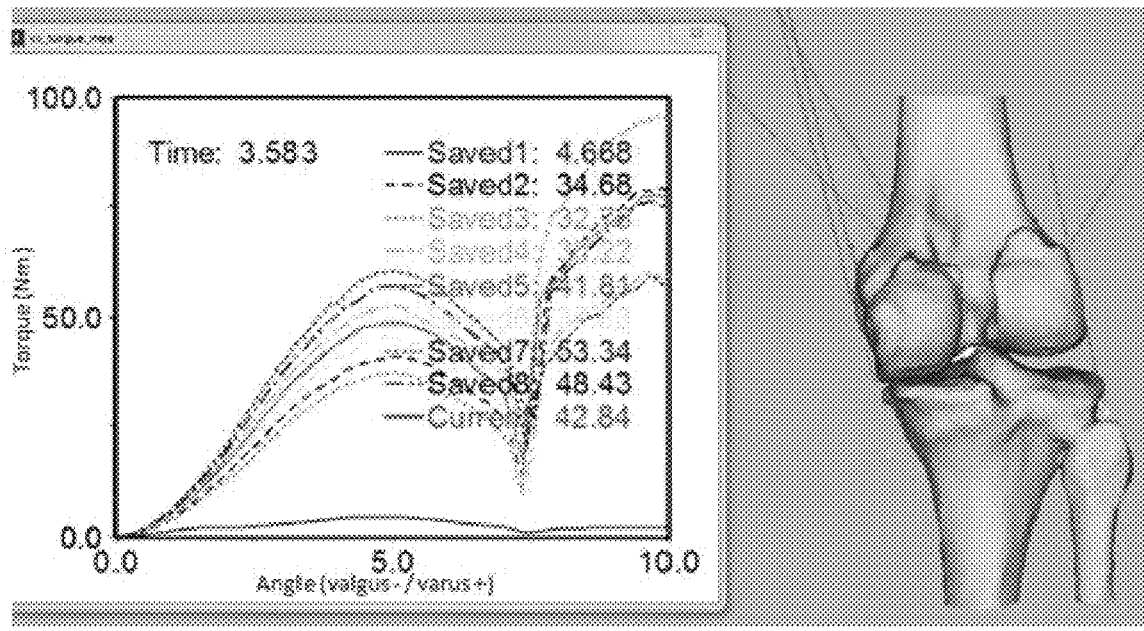
FIG. 31 illustrates an example of the optimization model that is optimised to determine the mechanical characteristic of the ligaments.

FIG. 31 illustrates an example of the optimization model that is optimised to determine the mechanical characteristic of the ligaments. In this example, from X-ray image data the joint is at 5° varus when flexed at 20°. The ligament optimization model may iteratively change ligament stiffness and free length value to achieve equilibrium at that position. The determined ligament properties to be used later are then the values at the equilibrium.

The ligament properties together with implants position and geometry 910 and patient geometry data from patient geometry module 904 are forwarded to a post-operative laxity prediction module 912, which determines a post-operative laxity 912, such as varus at extension, valgus at extension, varus at 90° flexion and valgus at 90° flexion and a graphical representation 914 of these characteristics. These results are sent to a reporting module 916, which generates the report as described above in relation to FIGS. 5 to 8.

Figure 32:
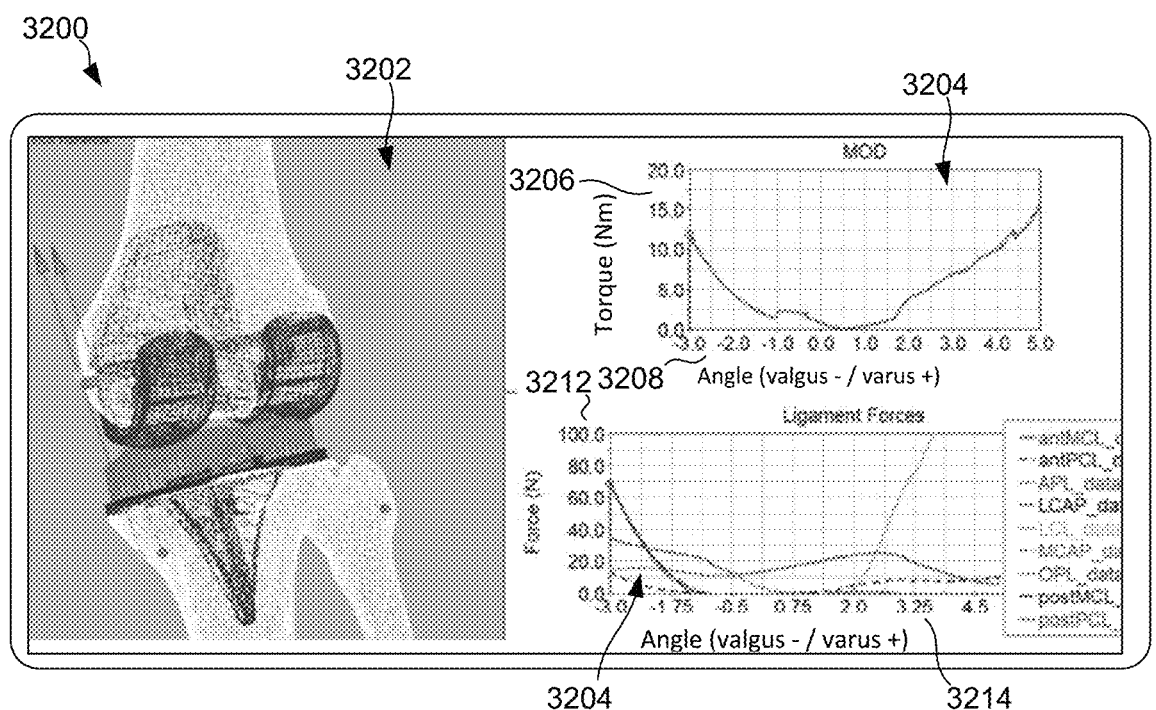
FIG. 32 illustrates an example of a post-op laxity assessment simulation display.

FIG. 32 illustrates an example of a post-op laxity assessment simulation display 3200 comprising a three-dimensional graphical representation 3202 of the knee, which may be animated to indicate angle of flexion or angle of valgus/varus, for example. Display 3200 further comprises a first graph 3204 indicating the torque 3206 applied to the mechanical model and the resulting valgus/varus angle 3208. Display 3200 also comprises a second graph 3210 indicating the resulting simulated ligament forces 3212 of each of the multiple ligaments in the knee over the valgus/varus angle 3214, where each line in second graph 3210 represents a different ligament. Display 3200 may be provided to a surgeon during the planning phase of the surgery, such as on a screen in the consulting room of the surgeon or on a screen in theatre.

While some examples herein relate to image data that represents the movement of the bones relative to each other, it is to be understood that different measurement data may also be used, such as a direct measurement of the movement of the bones under load by measuring the positions of landmarks that are accessible through the skin or even during surgery, such as by measuring the distances from the medial or lateral condyle using a surgical calliper without the use of X-ray or other images. These methods therefore provide contact-based data since these methods are based on contacting the bones either directly or through the skin.

Further, the measurement data used to determine the mechanical properties of the ligaments may be reported computer assisted surgery data, such as kinematics between bones captured by a navigation system the as surgeon assesses the joint with various movements.

Figure 33A:
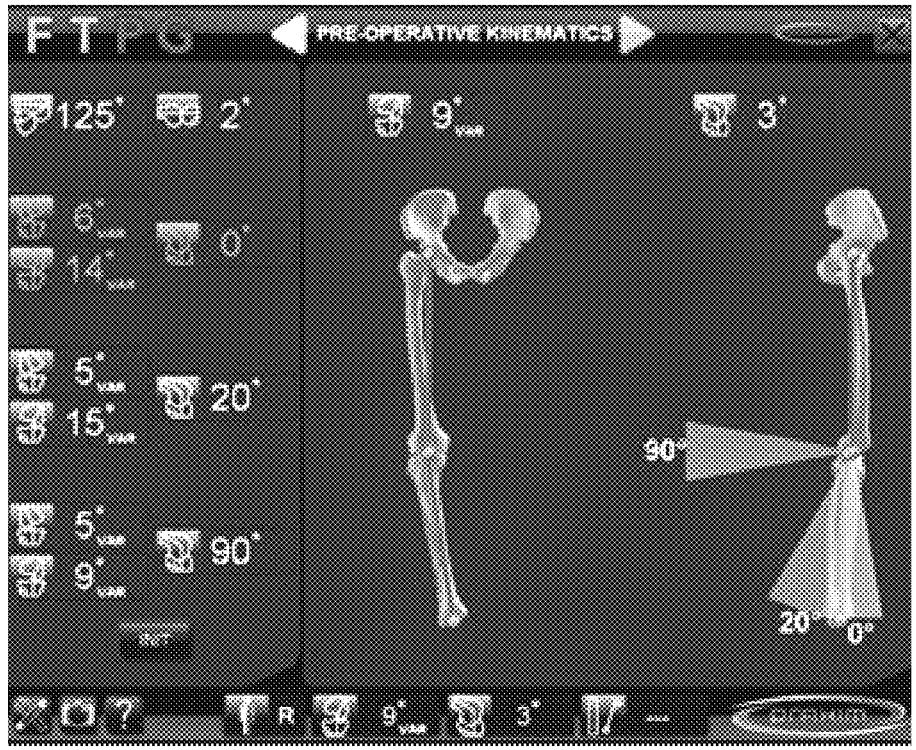
FIGS. 33a and 33b illustrate an example of a navigation system that provides different measurement data, such as varus/valgus at different flexion angles.
Figure 33B:
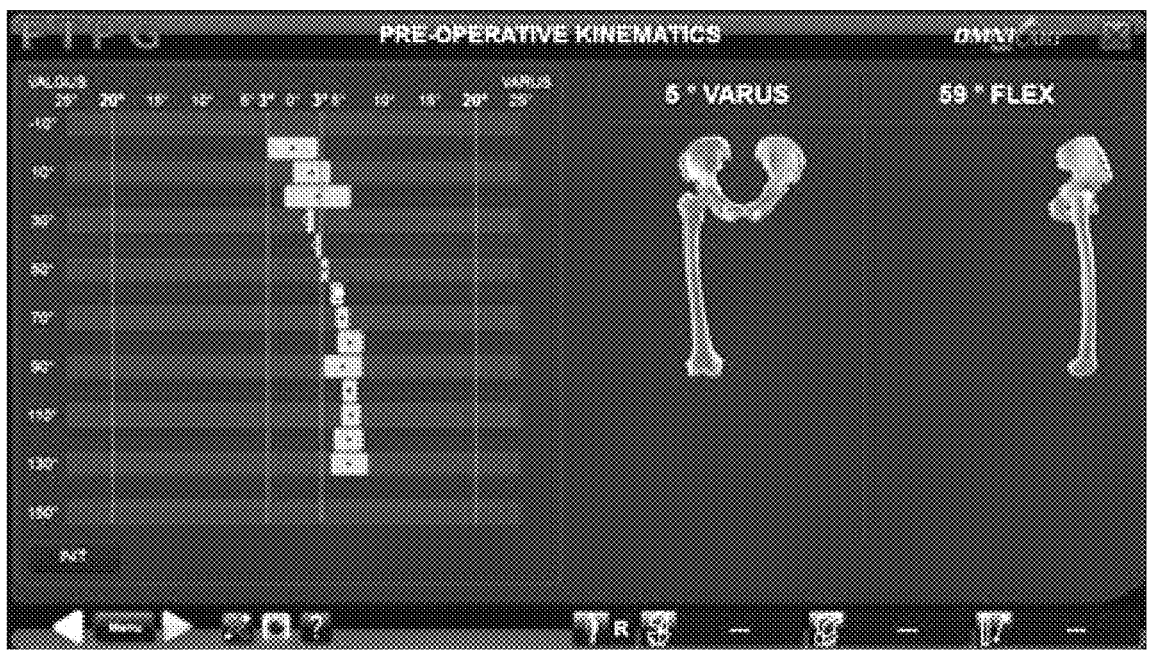

FIGS. 33a and 33b illustrate an example of a navigation system that provides different measurement data, such as varus/valgus at different flexion angles.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices. It is noted that while the above examples relate to knee surgeries, methods and systems described herein may equally be applicable to other clinical procedures, such as hip replacements.

The present embodiments are, therefore, to be considered in all respects as illustrative and not restrictive.

The invention claimed is:

1. A method for assisting a surgeon with a graphical representation of a dynamic knee score for a knee surgery, the method comprising:
receiving computer tomography data of a current patient's knee and building a 3D model of the patient's knee to represent the computer tomography data;
receiving user input from the surgeon, the user input comprising an identifier of a knee implant, the knee implant comprising a tibial component;
retrieving multiple machine learning model parameters indicative of machine learning performed on historical patient records, the historical patient records comprising multiple historical kinematic parameters of each of multiple historical patients as inputs and a reported patient outcome for each historical patient as output, the machine learning model parameters being indicative of a relationship between the multiple historical kinematic parameters and the reported patient outcome;
for each of multiple values of rotation of the tibial component and slope of the tibial component:
configuring a post-operative kinematic model of the current patient's knee based on the computer tomography data, the user input and that value of the rotation and the slope, wherein configuring the post-operative kinematic model comprises:
virtually performing the surgery by introducing cut surfaces to change a shape of bones in the 3D model and adding a shape of the knee implant; and
simplifying the 3D model to the post-operative kinematic model;

performing a kinematic simulation based on the post-operative kinematic model to determine multiple simulated kinematic parameters; and estimating a current patient outcome by applying the multiple machine learning model parameters to the multiple simulated kinematic parameters of the current patient; and generating a shaded surface spanning the multiple values of rotation of the tibial component and slope of the tibial component on a user interface to graphically represent the estimated current patient outcome for each of the multiple values of rotation of the tibial component and slope of the tibial component.

2. The method of claim 1, wherein the multiple historical kinematic parameters are indicative of a kinematic simulation of the historical patients' knees.

3. The method of claim 1, wherein the method further comprises performing the machine learning on the historical patient records.

4. The method of claim 3, wherein performing the machine learning comprises selecting the multiple historical kinematic parameters from a larger set of potential kinematic parameters.

5. The method of claim 3, further comprising receiving from each of the multiple historical patients the reported outcome as user input via a user interface.

6. The method of claim 1, wherein the multiple historical kinematic parameters and the multiple simulated kinematic parameters are independent of a knee implant geometry.

7. The method of claim 1 further comprising determining one or more simulated kinematic parameters that are most responsible for the current patient outcome.

8. The method of claim 1, further comprising generating one shaded surface for each of multiple surgery parameters by repeating the following steps (a) and (b) for each of the multiple surgery parameters:

(a) for each of multiple values of rotation of the tibial component and slope of the tibial component performing the following steps (a1), (a2), and (a3):

(a1) configuring a post-operative kinematic model of the current patient's knee based on the computer tomography data, the user input and that value of the rotation and the slope and that surgery parameter;

(a2) performing a kinematic simulation based on the post-operative kinematic model to determine multiple simulated kinematic parameters;

(a3) estimating a current patient outcome by applying the multiple machine learning model parameters to the multiple simulated kinematic parameters of the current patient; and (b) generating a shaded surface for that surgery parameter, spanning the multiple values of rotation of the tibial component and slope of the tibial component on a user interface to graphically represent the estimated current patient outcome for each of the multiple values of rotation of the tibial component and slope of the tibial component.

9. The method of claim 8, further comprising arranging the shaded surface for each of the multiple surgery parameters in a grid on a user interface to indicate combinations of surgery parameters.

10. The method of claim 1, wherein the reported patient outcome is based on Patient Reported Outcome Measures.

11. The method of claim 1, wherein the reported patient outcome is based on a percentile within the historical patients.

12. The method of claim 1, wherein the historical patient records further comprise historical anatomical measurements;

the multiple machine learning model parameters are indicative of a relationship between the historical anatomical measurements and the reported patient outcome; and estimating the current patient outcome comprises applying the multiple machine learning model parameters to anatomical measurements of the current patient's knee.

13. The method of claim 1, wherein the historical patient records further comprise historical demographic parameters and patient questionnaire data capture parameters;

the machine learning model parameters are indicative of a relationship between (i) the historical demographic parameters and patient questionnaire data capture parameters and iii) the reported patient outcome; and estimating the current patient outcome comprises applying the multiple machine learning model parameters to a current patient's demographic and patient questionnaire data capture parameters.

14. The method of claim 1, wherein estimating the current patient outcome is based on kinematic expert knowledge to either modify or reweight penalty factors from the kinematic simulation or is based on new penalty factors from the kinematic simulation.

15. The method of claim 14, wherein the kinematic expert knowledge is different for different users of a computer system performing the method.

16. The method of claim 1, further comprising determining further placement input parameters of the knee implant based on the simulated kinematic parameters other than slope and rotation of the tibial component in order to optimize the estimated current patient outcome.

17. A non-transitory computer readable medium with program code stored thereon that is configured to cause, when executed by a computer, the computer to perform the method of claim 1.

18. A computer system for assisting a surgeon with a graphical representation of a dynamic knee score for a knee surgery, the computer system comprising:

a data input port configured to receive computer tomography data of a current patient's knee;

a user input device configured to receive user input from the surgeon, the user input comprising an identifier of a knee implant, the knee implant comprising a tibial component;

a data source connection configured to retrieve multiple machine learning model parameters indicative of a machine learning performed on historical patient records, the historical patient records comprising multiple historical kinematic parameters of each of multiple historical patients as inputs and a reported patient outcome for each historical patient as output, the machine learning model parameters being indicative of a relationship between the multiple historical kinematic parameters and the reported patient outcome;

a processor; a data storage device with program code stored thereon, wherein the program code is configured to perform the steps of:

building a 3D model of the patient's knee to represent the computer tomography data;

for each of multiple values of rotation of the tibial component and slope of the tibial component:

configuring a post-operative kinematic model of the current patient's knee based on the computer tomography data, the user input and that value of the rotation and the slope, wherein configuring the post-operative kinematic model comprises:
  virtually performing the surgery by introducing cut surfaces to change a shape of bones in the 3D model and adding a shape of the knee implant; and
  simplifying the 3D model to the post-operative kinematic model;
performing a kinematic simulation based on the post-operative kinematic model to determine multiple simulated kinematic parameters; and
estimating a current patient outcome by applying the multiple machine learning model parameters to the multiple simulated kinematic parameters of the current patient; and
generating a shaded surface spanning the multiple values of rotation of the tibial component and slope of the tibial component on a user interface to graphically represent the estimated current patient outcome for each of the multiple values of rotation of the tibial component and slope of the tibial component.

19. The computer system of claim 18, further comprising a display device to display the shaded surface to the surgeon.

* * * * *